US008993744B2

(12) United States Patent
Ross et al.

(10) Patent No.: US 8,993,744 B2
(45) Date of Patent: Mar. 31, 2015

(54) UNIVERSAL DENGUE VIRUS SEQUENCES AND METHODS OF USE

(75) Inventors: Ted M. Ross, Pittsburgh, PA (US); Nikolaos Vasilakis, Galveston, TX (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 171 days.

(21) Appl. No.: 13/698,719

(22) PCT Filed: May 23, 2011

(86) PCT No.: PCT/US2011/037598
§ 371 (c)(1),
(2), (4) Date: Nov. 19, 2012

(87) PCT Pub. No.: WO2011/146933
PCT Pub. Date: Nov. 24, 2011

(65) Prior Publication Data
US 2013/0071419 A1    Mar. 21, 2013

Related U.S. Application Data

(60) Provisional application No. 61/396,082, filed on May 21, 2010.

(51) Int. Cl.
*C07H 21/02* (2006.01)
*A61K 39/12* (2006.01)
*C07K 19/00* (2006.01)
*C07K 14/005* (2006.01)
*A61K 39/00* (2006.01)

(52) U.S. Cl.
CPC ............... *A61K 39/12* (2013.01); *C07K 19/00* (2013.01); *C07K 14/005* (2013.01); *C12N 2770/24122* (2013.01); *C12N 2770/24171* (2013.01); *A61K 2039/5258* (2013.01); *A61K 2039/53* (2013.01); *A61K 2039/55516* (2013.01); *A61K 2039/70* (2013.01); *C07K 2319/00* (2013.01); *C12N 2770/24123* (2013.01); *C12N 2770/24134* (2013.01)
USPC ..................................... 536/23.72; 424/218.1

(58) Field of Classification Search
None
See application file for complete search history.

(56) References Cited

U.S. PATENT DOCUMENTS

| 6,455,509 B1 | 9/2002 | Kochel et al. |
| 2006/0018928 A1 | 1/2006 | Pang |
| 2006/0073164 A1 | 4/2006 | Tangy et al. |
| 2009/0074781 A1 | 3/2009 | Chen et al. |
| 2009/0197320 A1 | 8/2009 | Fan |
| 2009/0312190 A1 | 12/2009 | Chinea Santiago et al. |
| 2010/0226924 A1 | 9/2010 | Tangy et al. |

FOREIGN PATENT DOCUMENTS

| CN | 101 308 137 | 11/2008 |
| WO | WO 01/39802 | 6/2001 |
| WO | WO 02/081754 | 10/2002 |
| WO | WO 2006/078657 | 7/2006 |
| WO | WO 2007/103322 | 9/2007 |
| WO | WO 2009/099716 | 8/2009 |
| WO | WO 2009/128949 | 10/2009 |
| WO | WO 2009/130261 | 10/2009 |

OTHER PUBLICATIONS

Jarman et al., "Microevolution of Dengue Viruses Circulating among Primary School Children in Kamphaeng Phet, Thailand," *J. Virol.*, vol. 82(11):5494-5500, 2008.
Klungthong et al., "The Molecular Epidemiology of Dengue Virus Serotype 4 in Bangkok, Thailand," *Virol.*, vol. 329(1):168-179, 2004.
Kochel et al., "Molecular Epidemiology of Dengue Virus Type 3 in Northern South America: 2000-2005," *Infection, Genetics and Evolution*, vol. 8(5):682-688, 2008.
Shu et al., "Molecular Characterization of Dengue Viruses Imported into Taiwan During 2003-2007: Geographic Distribution and Genotype Shift," *Am. J. Trop. Med. Hyg.*, vol. 80(6):1039-1046, 2009.
Wittke et al., "Extinction and Rapid Emergence of Strains of Dengue 3 Virus during an Interepidemic Period," *Virol.*, vol. 301(1):148-156, 2002.
Zhang et al., "Clade Replacements in Dengue Virus Serotypes 1 and 3 are Associated with Changing Serotype Prevalence," *J. Virol.*, vol. 79(24):15123-15130, 2005.
Supplementary European Search Report for EP 11 78 4388, dated Nov. 8, 2013.
Dunn et al., Enhancement of anti-DIII Antibodies by the C3d Derivative P28 Results in Lower Viral Titers and Augments Protection in Mice, *Virol. J.*, vol. 7:95-102, 2010.
GenBank Accession No. AF425619, Jun. 19, 2003.
GenBank Accession No. 1C3D_A, Sep. 24, 2008.
GenBank Accession No. AAN32776, Jun. 19, 2003.
GenBank Accession No. P14337.2 (GI:119364638), Apr. 20, 2010.

*Primary Examiner* — Stacy B Chen
(74) *Attorney, Agent, or Firm* — Klarquist Sparkman, LLP

(57) ABSTRACT

Disclosed herein are computationally optimized broadly reactive dengue virus E polypeptide sequences for DENV-1, DENV-2, DENV-3 and DENV-4. Also disclosed are dengue virus E protein fragments (such as the E protein ectodomain and DIII domain) fused to the molecular adjuvant P28. The disclosed nucleic acid and polypeptide sequences can be used as vaccines for immunization against dengue virus infection. In some cases, the vaccine includes a virus-like particle containing the universal dengue virus E protein, or fragment thereof, or the vaccine is a DNA molecule encoding the VLP.

11 Claims, 11 Drawing Sheets

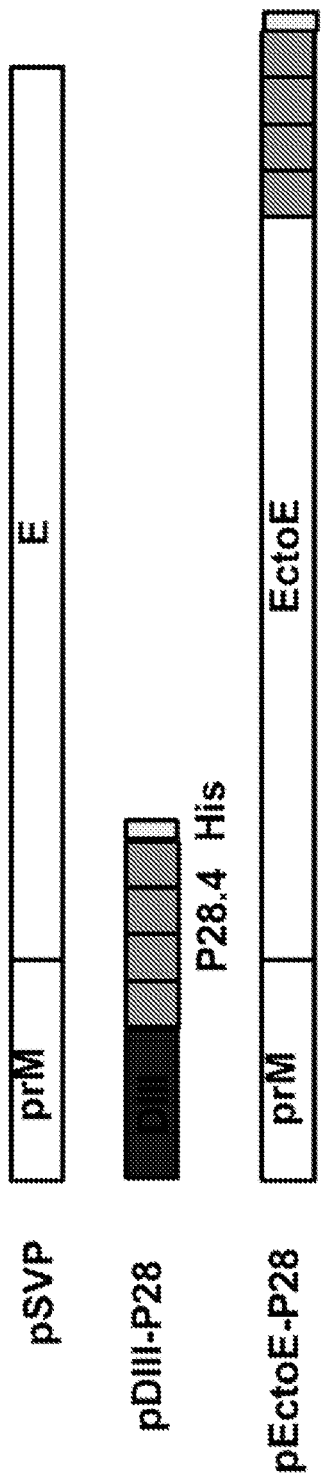
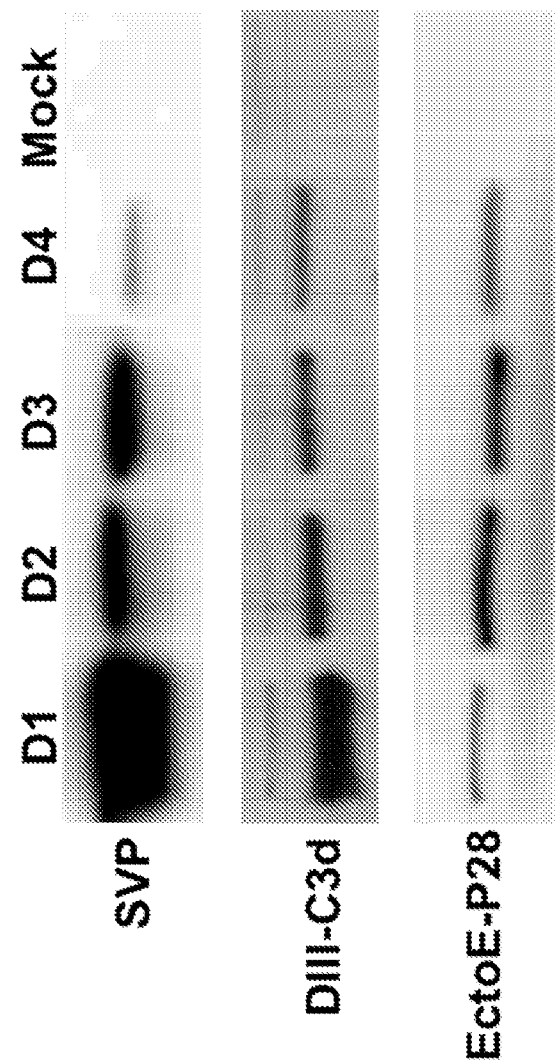
FIG. 1A
FIG. 1B

Tetravalent vaccine

Dengue 1

FIG. 7B
Dengue 2

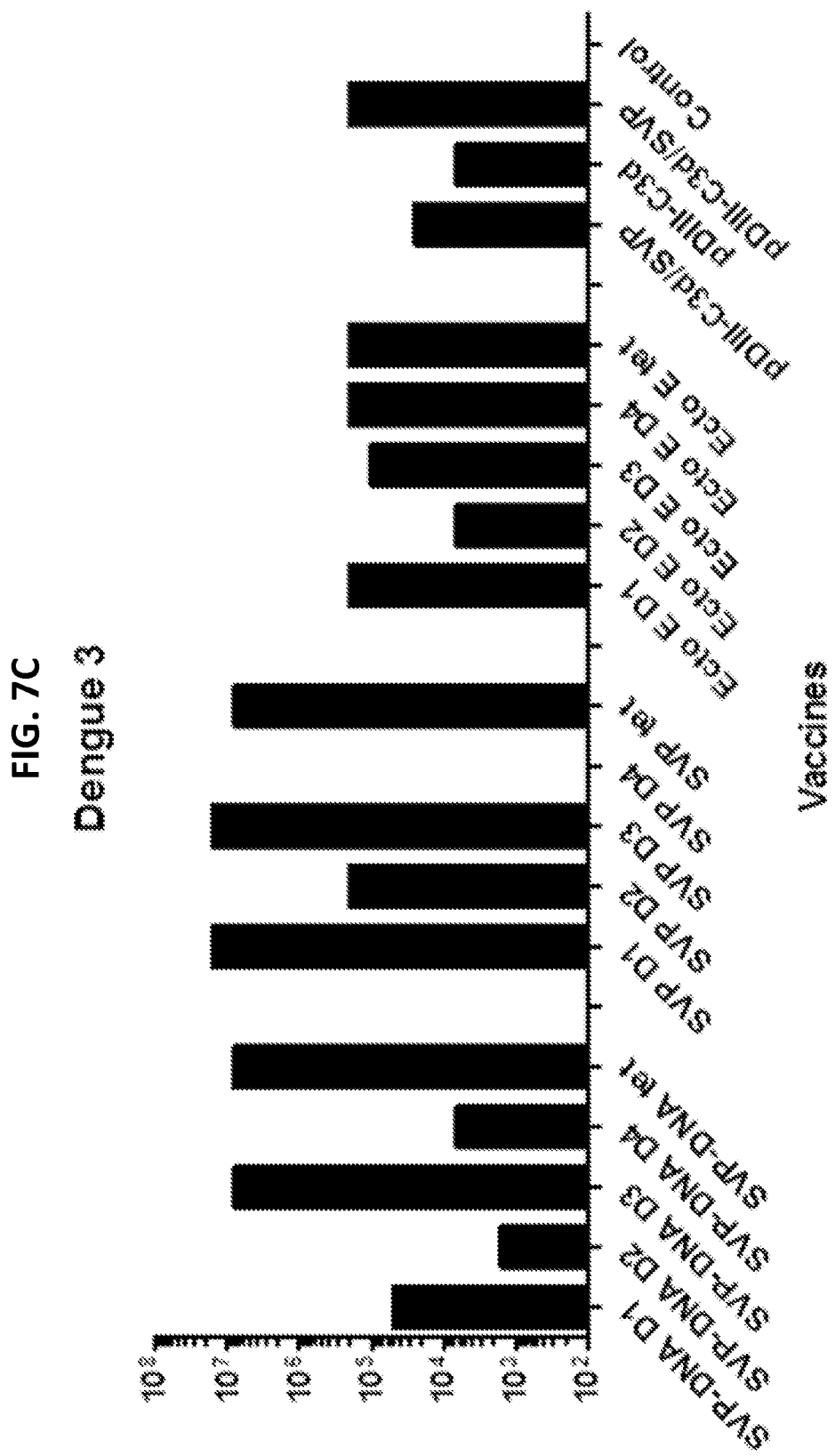

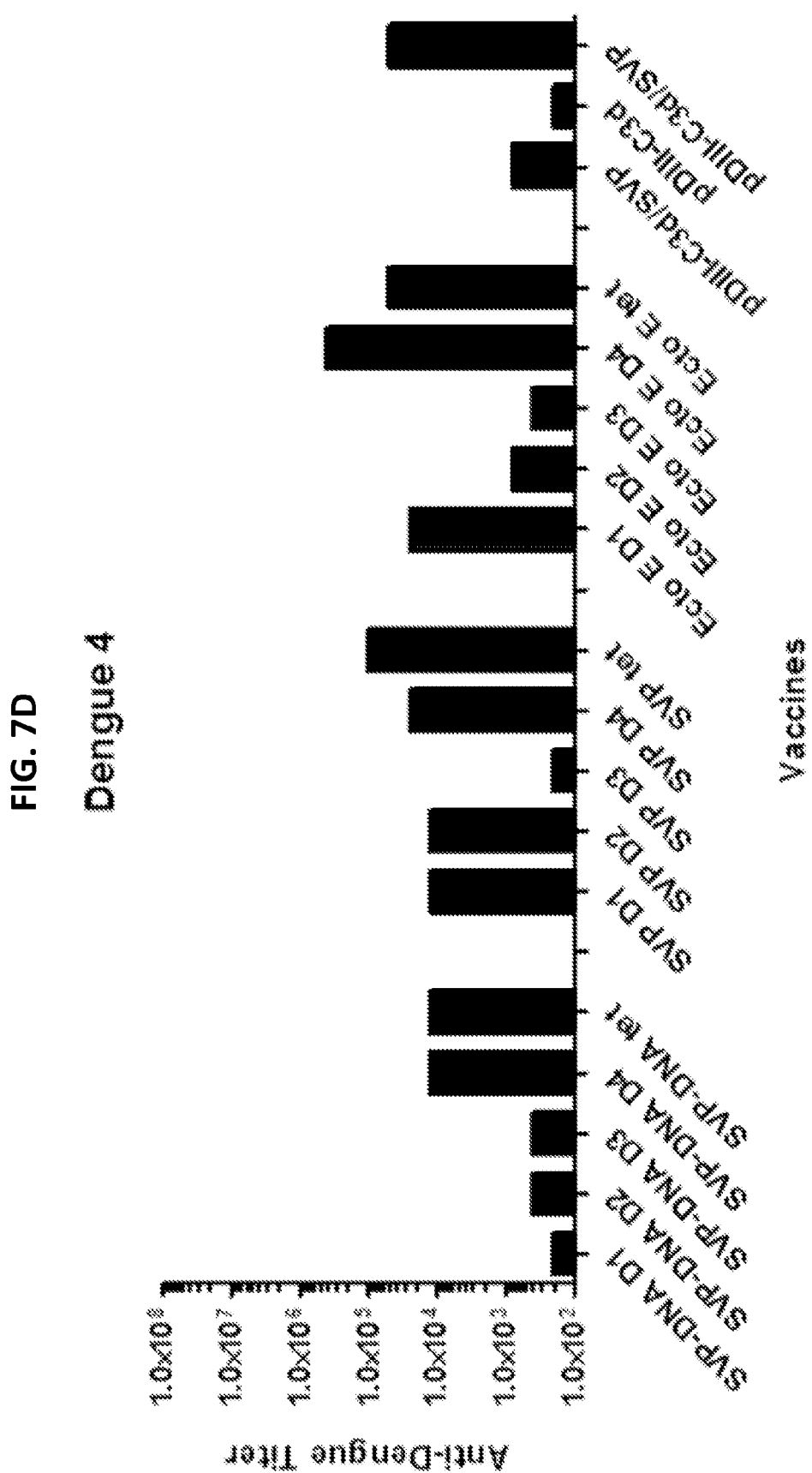
FIG. 7D Dengue 4

FIG. 7E
West Nile

UNIVERSAL DENGUE VIRUS SEQUENCES AND METHODS OF USE

CROSS REFERENCE TO RELATED APPLICATIONS

This is the U.S. National Stage of International Application No. PCT/US2011/037598, filed May 23, 2011, which was published in English under PCT Article 21(2), which in turn claims the benefit of U.S. Provisional Application No. 61/396,082, filed May 21, 2010, which is herein incorporated by reference in its entirety.

FIELD

This disclosure is related to the field of virology, specifically to the filed of synthetic dengue virus antigens and their use to produce an immune response.

BACKGROUND

Flaviviruses are significant human pathogens for which no commercially approved vaccines exist. Flaviviruses exist as small (50 nm) icosahedral particles containing a single RNA molecule encoding 3 structural proteins (C, M and E) that make up the virion, and 7 nonstructural proteins required for genome replication. This virus family includes a number of mosquito-borne viruses that are pathogenic for humans, including West Nile virus (WNV), dengue virus (DENV), Japanese encephalitis virus (JEV), and yellow fever virus (YFV). Each virus is endemic in regions with a large and highly susceptible population, causing significant medical and economic burden.

DENV has four known serotypes (1-4) that have defined global distribution. However, modern travel has altered the pattern and introduced DENV into naive populations. Over the past 50 years, dengue virus has become the most significant arbovirus human pathogen in the world because of its unusual transmission cycle involving a human host for amplification. There are currently 2.5 billion people living in dengue endemic regions with roughly 100 million annual cases of dengue fever and hundreds of thousands of cases of dengue hemorrhagic fever and dengue shock syndrome (Gubler, *Clin. Microbiol. Rev.* 11:480-496, 1998).

No vaccines are currently commercially available against any of the four DENV serotypes (DENV 1-4) largely because vaccine production is hampered by the fact that neutralizing antibodies to one serotype do not effectively neutralize the remaining DENV serotypes (Halstead and O'Rourke, *J. Exp. Med.* 146:201-217, 1977). In fact, low levels of these antibodies may actually increase the risk for more severe disease during secondary infection due to a phenomenon known as antibody dependent enhancement (ADE), which occurs when antibodies against one DENV serotype bind in a non-neutralizing manner to DENV particles of another serotype. This binding allows increased infection of Fc receptor-bearing cells, such as macrophages, which can change the infection profile of the virus or cause a release of chemokines leading to dengue hemorrhagic fever or dengue shock syndrome (Halstead and O'Rourke, *J. Exp. Med.* 146:201-217, 1977). Thus, a need exists for the development of a broadly protective dengue virus vaccine.

SUMMARY

Disclosed herein are computationally optimized broadly reactive (referred to herein as "universal" or "consensus") dengue virus E polypeptide sequences for DENV-1, DENV-2, DENV-3 and DENV-4. Also disclosed are dengue virus E protein fragments (such as the E protein ectodomain and DIII domain) fused to the molecular adjuvant P28. The disclosed nucleic acid and polypeptide sequences can be used as vaccines for eliciting an immune response against dengue virus.

Provided herein are isolated nucleic acid molecules that include a nucleotide sequence encoding a dengue virus E protein, or a fragment thereof. In some embodiments, the dengue virus E protein is a universal dengue virus E protein for DENV-1, DENV-2, DENV-3 or DENV-4. In other embodiments, the dengue virus E protein fragment comprises the E protein ectodomain of the universal dengue virus E protein for DENV-1, DENV-2, DENV-3 or DENV-4. In other embodiments, the E protein fragment is the DIII domain of DENV-1, DENV-2, DENV-3 or DENV-4. In some embodiments, the nucleic acid molecules further encode a dengue virus prM protein. Further provided are vectors comprising the nucleic acid molecules, and isolated cells comprising the vectors.

Also provided are isolated dengue virus E proteins, or fragments thereof. In some embodiments, the dengue virus E protein is a universal dengue virus E protein derived from DENV-1, DENV-2, DENV-3 or DENV-4. In other embodiments, the E protein fragment is the E protein ectodomain of the universal dengue virus E protein of DENV-1, DENV-2, DENV-3 or DENV-4. In yet other embodiments, the E protein fragment is the DIII domain of DENV-1, DENV-2, DENV-3 or DENV-4. Further provided are VLPs comprising a universal dengue virus E protein, or fragment thereof. In some cases, the VLP further includes a dengue virus prM protein. Also provided are fusion proteins comprising a universal dengue virus E protein, or fragment thereof.

Compositions comprising the disclosed nucleic acid molecules, vectors, dengue virus E proteins (and fragments thereof), VLPs and fusion proteins are also provided by the present disclosure. In some embodiments, the composition is a tetravalent composition comprising DENV-1, DENV-2, DENV-3 and DENV-4 universal E proteins, or nucleic acid molecules encoding the four universal E proteins.

Further provided are methods of eliciting an immune response by administration of a nucleic acid molecule, vector, dengue virus E protein (or fragment thereof), VLP or fusion protein as disclosed herein. In some embodiments, the method includes administration of a single type of dengue virus E protein, or fragment thereof. In other embodiments, the method includes administration of a tetravalent composition including E proteins (or fragments thereof) derived from all four dengue virus serotypes.

Also provided are methods of immunizing a subject against dengue virus infection by administration of a VLP, or a DNA molecule encoding a VLP, as disclosed herein. In some embodiments, the method of immunization includes administration of a composition including a VLP from a single serotype of dengue virus (i.e. a DENV-1, DENV-2, DENV-3 or DENV-4 VLP). In other embodiments, the method of immunization includes administration of VLPs from all four dengue virus serotypes (i.e., DENV-1, DENV-2, DENV-3 and DENV-4 VLPs).

The foregoing and other features and advantages will become more apparent from the following detailed description of several embodiments, which proceeds with reference to the accompanying figures.

BRIEF DESCRIPTION OF THE FIGURES

FIGS. 1A and 1B show a schematic diagram of constructs and expression of vaccine plasmids. (A) Shown are a diagram of the four Dengue subtype prM-E gene segments of the pSVP constructs (top), the segments used in the DIII-P28 constructs (middle) and the pEctoE-P28 constructs (bottom). The DIII region of the E gene (amino acids 586-705) was cloned downstream of the tpA leader sequence, and in some cases, P28 was also cloned in frame and directly after the 3' end of the DIII gene. An artificial BamHI site and stop codon was engineered at position 705 in the E gene to create the truncated Ecto E gene, and P28 was cloned into the Ecto E construct using the BamHI site to create the Ecto E-P28 construct. (B) Supernatants from 293T cells transiently transfected with plasmid DNA expressing the SVP, DIII-P28, or the Ecto E-P28 proteins in the supernatants from each of the four subtypes (D1, D2, D3 and D4) of Dengue were assessed by SDS-PAGE and Western blot.

FIG. 2 is a schematic diagram and tables showing vaccine timeline, vaccines, and doses.

FIG. 3 shows vaccine elicited antibodies by intradermal gene gun vaccination. Total IgG titers were measured by ELISA on Dengue DIII-coated plates from mice vaccinated by gene gun with DNA plasmids encoding sections of the Dengue E gene, with or without molecular adjuvant P28 on week 8. Each dot represents an individual mouse. Undetectable antibody titers were arbitrarily assigned a titer of 1. Error bars denote the standard error within the samples with a measurable titer. Representative data from 1 of 2 experiments is shown. Tables show semi-quantitative representation of the data.

FIG. 4 shows vaccine elicited antibodies by purified SVP following intramuscular injection. Total IgG titers were measured by ELISA on Dengue DIII-coated plates from mice vaccinated intramuscular with purified SVPs on week 8. Each dot represents an individual mouse. Undetectable antibody titers were arbitrarily assigned a titer of 1. Error bars denote the standard error within the samples with a measurable titer. Representative data from 1 of 2 experiments is shown. The table shows the dose of each SVP.

FIG. 5 is a table showing IgG isotypes following vaccination, Relative IgG isotypes (IgG1, IgG2a, IgG2b, IgG3) were determined using a 1:100 dilution of each vaccine elicited antisera. Each dot represents an individual mouse. Undetectable antibody titers were arbitrarily assigned a titer of 1. Error bars denote the standard error within the samples with a measurable titer. Representative data from 1 of 2 experiments is shown. A 2-way unmatched ANOVA with a Bonferroni post-test was used to determine the significance of the data between groups, which is denoted by asterisks; * $P<0.05$,  $P<0.01$, * $P<0.001$.

FIG. 6 shows vaccine elicited antibodies by a tetravalent mixture of all 4 Dengue purified SVPs following intramuscular injection. Total IgG titers were measured by ELISA on Dengue DIII-coated plates from mice vaccinated intramuscularly with all four purified SVPs on week 8. Each dot represents an individual mouse. Undetectable antibody titers were arbitrarily assigned a titer of 1. Error bars denote the standard error within the samples with a measurable titer. Representative data from 1 of 2 experiments is shown.

Figure 7B:
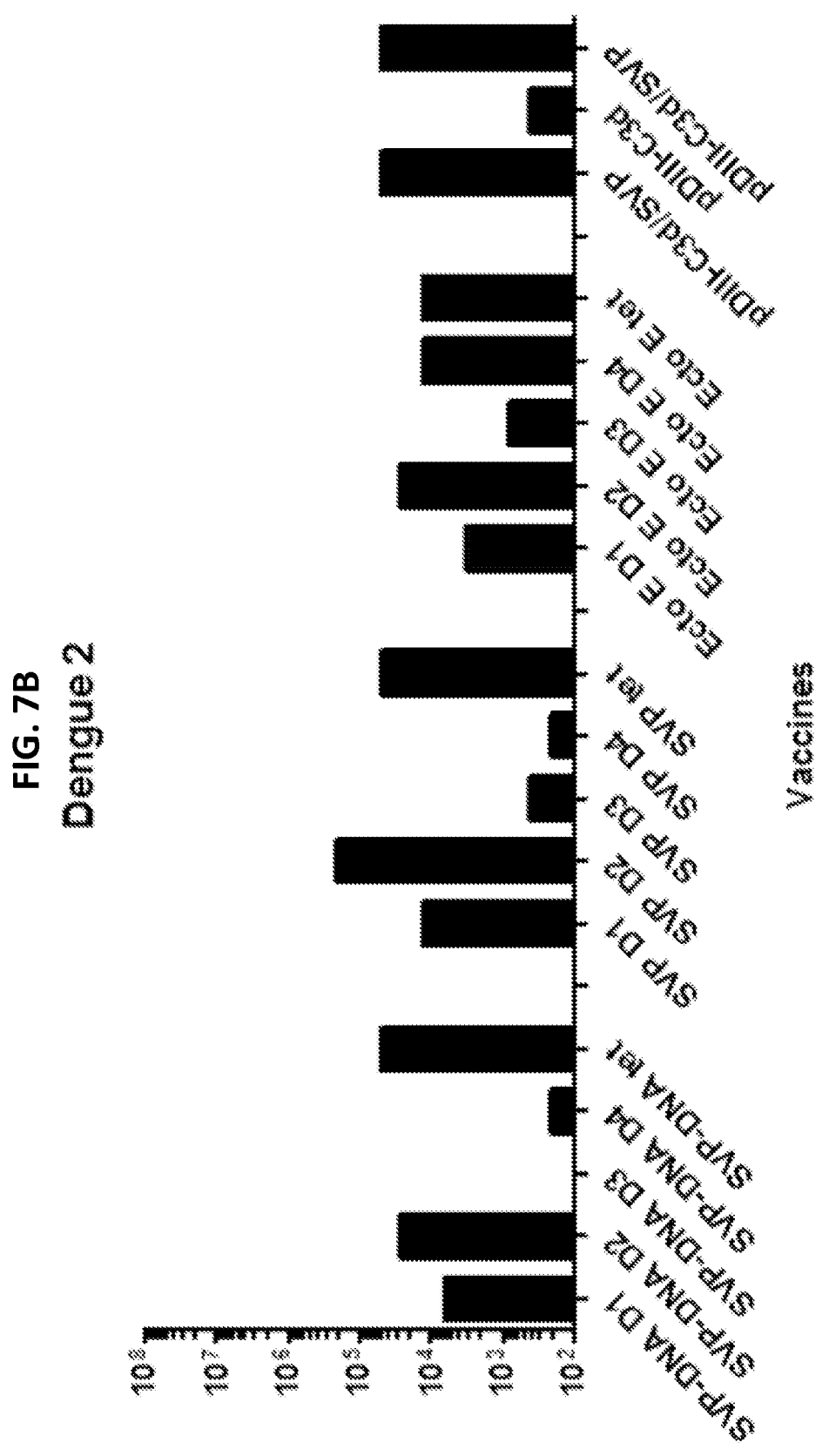
Figure 7E:
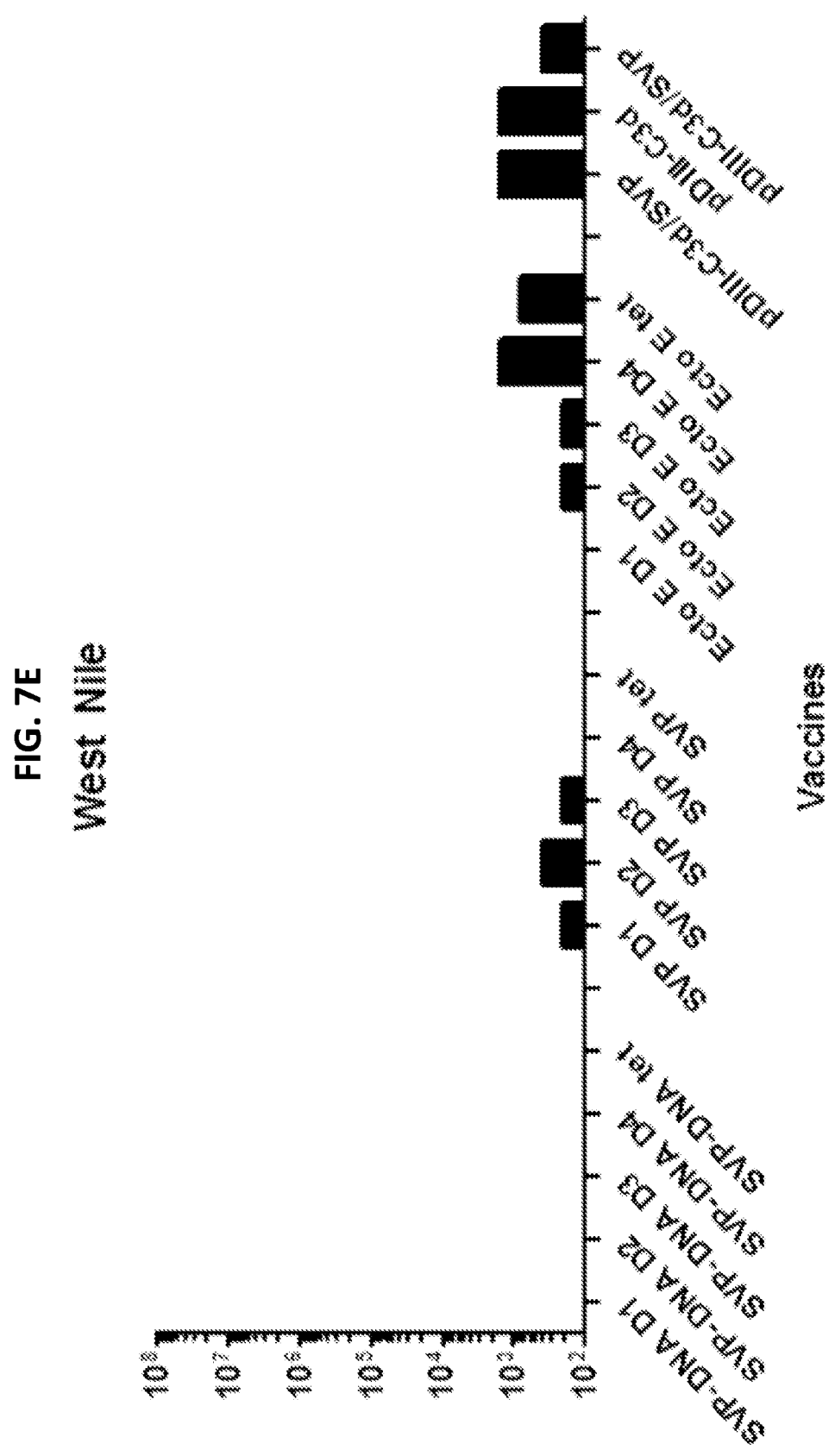

FIGS. 7A-7E are graphs showing individual cross-reactive ELISA titers against Dengue 1 (A), Dengue 2 (B), Dengue 3 (C), Dengue 4 (D) and WNV (E) full length E protein. Total IgG titers were measured by ELISA on E protein coated plates from mice vaccinated intramuscularly with all dengue vaccine candidates on week 8.

SEQUENCE LISTING

The nucleic and amino acid sequences listed are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Oct. 29, 2012, 70.3 KB, which is incorporated by reference herein. In the accompanying sequence listing:

SEQ ID NO: 1 is the nucleotide sequence of the DENV-1 consensus E protein coding sequence.

SEQ ID NO: 2 is the amino acid sequence of the DENV-1 consensus E protein.

SEQ ID NO: 3 is the nucleotide sequence of the DENV-2 consensus E protein coding sequence.

SEQ ID NO: 4 is the amino acid sequence of the DENV-2 consensus E protein.

SEQ ID NO: 5 is the nucleotide sequence of the DENV-3 consensus E protein coding sequence.

SEQ ID NO: 6 is the amino acid sequence of the DENV-3 consensus E protein.

SEQ ID NO: 7 is the nucleotide sequence of the DENV-4 consensus E protein coding sequence.

SEQ ID NO: 8 is the amino acid sequence of the DENV-4 consensus E protein.

SEQ ID NO: 9 is the nucleotide sequence of a construct (DENV-1_ss-prM-consE.fa) containing the DENV-1 consensus E protein coding sequence.

SEQ ID NO: 10 is the nucleotide sequence of a construct (DENV-2 (NGC) NheI-kozak-SS-prM/E-XhoI in pcDNA3.1 (+)) containing the DENV-2 consensus E protein coding sequence.

SEQ ID NO: 11 is the nucleotide sequence of a construct (DENV3_(H87)_ss_prM_consE_Xba.fa) containing the DENV-3 consensus E protein coding sequence.

SEQ ID NO: 12 is the nucleotide sequence of a construct (H241_EcoRI-kozak-ss-prM-consE-.fa) containing the DENV-4 consensus E protein coding sequence.

SEQ ID NO: 13 is the nucleotide sequence of DENV-1 DIII.

SEQ ID NO: 14 is the amino acid sequence of DENV-1 DIII.

SEQ ID NO: 15 is the nucleotide sequence of DENV-2 DIII.

SEQ ID NO: 16 is the amino acid sequence of DENV-2 DIII.

SEQ ID NO: 17 is the nucleotide sequence of DENV-3 DIII.

SEQ ID NO: 18 is the amino acid sequence of DENV-3 DIII.

SEQ ID NO: 19 is the nucleotide sequence of DENV-4 DIII.

SEQ ID NO: 20 is the amino acid sequence of DENV-4 DIII.

SEQ ID NO: 21 is the amino acid sequence of the C3d peptide P28.

DETAILED DESCRIPTION

I. Abbreviations

ADE antibody-dependent enhancement
APC antigen presenting cell
COBRA codon-optimized broadly reactive antigen
DENY dengue virus
DF dengue fever
DHF dengue hemorrhagic fever
DSS dengue shock syndrome
E envelope protein

Figure 2:
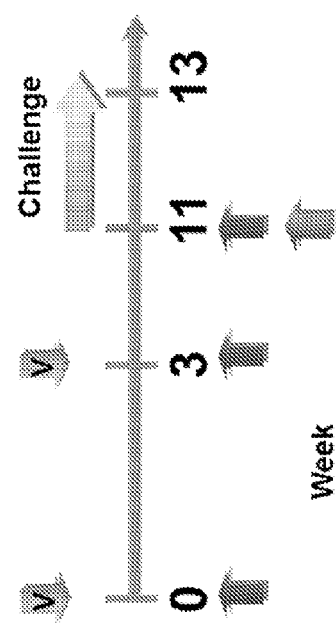

MHC major histocompatibility complex
prM premembrane protein
VLP virus-like particle
WNV West Nile virus II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, administering a composition to a subject means to give, apply or bring the composition into contact with the subject. Administration can be accomplished by any of a number of routes, such as, for example, topical, oral, subcutaneous, intramuscular, intraperitoneal, intravenous, intrathecal and intradermal.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In some embodiments of the disclosed compositions and methods, the antigen is flavivirus E protein.

Codon-optimized: A "codon-optimized" nucleic acid refers to a nucleic acid sequence that has been altered such that the codons are optimal for expression in a particular system (such as a particular species of group of species). For example, a nucleic acid sequence can be optimized for expression in mammalian cells. Codon optimization does not alter the amino acid sequence of the encoded protein.

Conservative substitution: A substitution of one amino acid residue in a protein sequence for a different amino acid residue having similar biochemical properties. Typically, conservative substitutions have little to no impact on the activity of a resulting polypeptide. For example, ideally, a dengue virus protein including one or more conservative substitutions (for example no more than 2, 5, 10, 20, 30, 40, or 50 substitutions) retains the structure and function of the wild-type protein. A polypeptide can be produced to contain one or more conservative substitutions by manipulating the nucleotide sequence that encodes that polypeptide using, for example, standard procedures such as site-directed mutagenesis or PCR. In one example, such variants can be readily selected by testing antibody cross-reactivity or its ability to induce an immune response.

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Envelope glycoprotein (E protein): A flavivirus structural protein that mediates binding of flavivirus virions to cellular receptors on host cells. The flavivirus E protein is required for membrane fusion, and is the primary antigen that induces protective immunity to flavivirus infection. Flavivirus E protein affects host range, tissue tropism and viral virulence. The flavivirus E protein contains three structural and functional domains, DI, DII and DIII. In mature virus particles the E protein forms head to tail homodimers lying flat and forming a dense lattice on the viral surface. As used herein, E protein "fragments" include any fragments of the E protein that are still capable of eliciting an immune response (such as an antibody response). In some embodiments, the fragment comprises or consists of the E protein ectodomain, or comprises or consists of the DIII domain.

Flavivirus non-structural protein: There are seven non-structural (NS) proteins of a flavivirus, NS1, NS2A, NS2B, NS3, NS4A, NS4B, and NS5, which are encoded by the portion of the flavivirus genome that is 3' to the structural proteins. NS1 has been implicated in RNA replication and has been shown to be secreted from infected mammalian cells (Post et al., *Virus Res.* 18:291-302, 1991; Mackenzie et al., *Virology* 220:232-240, 1996; Muylaert et al., *Virology* 222: 159-168, 1996). NS1 can elicit strong humoral immune responses and is a potential vaccine candidate (Shlesinger et al., *J. Virol.* 60:1153-1155, 1986; Qu et al., *J. Gen. Virol.* 74:89-97, 1993). NS2 is cleaved into NS2A and NS2B, with the function of NS2A remaining unknown. NS2B forms a complex with NS3 and functions as a cofactor for the NS3 protease, which cleaves portions of the virus polyprotein. NS3 also functions as an RNA helicase and is used to unwind viral RNA during replication (Li et al., *J. Virol.* 73:3108-3116, 1999). While the exact functions of NS4A and NS4B remain to be elucidated, they are thought to be involved in RNA replication and RNA trafficking (Lindenbach and Rice, In: *Fields Virology*, Knipe and Howley, eds., Lippincott, Williams, and Wilkins, 991-1041, 2001). Finally, the NS5 protein is an RNA-dependent RNA polymerase involved in genome replication (Rice et al., *Science* 229:726-733, 1985). NS5 also shows methyltransferase activity commonly found in RNA capping enzymes (Koonin, *J. Gen. Virol.* 74:733-740, 1993).

Flavivirus structural protein: The capsid (C), premembrane (prM), and envelope (E) proteins of a flavivirus are the viral structural proteins. Flavivirus genomes consist of positive-sense RNAs that are roughly 11 kb in length. The genome has a 5' cap, but lacks a 3' polyadenylated tail (Wengler et al., *Virology* 89:423-437, 1978) and is translated into one polyprotein. The structural proteins (C, prM, and E) are at the amino-terminal end of the polyprotein followed by the non-structural proteins (NS1-5). The polyprotein is cleaved by virus and host derived proteases into individual proteins. The C protein forms the viral capsid while the prM and E proteins are embedded in the surrounding envelope (Russell et al., *The Togaviruses: Biology, Structure, and Replication*, Schlesinger, ed., Academic Press, 1980). The E protein functions in binding to host cell receptors resulting in receptor-mediated endocytosis. In the low pH of the endosome, the E protein undergoes a conformational change causing fusion between the viral envelope and the endosomal membranes. The prM protein is believed to stabilize the E protein until the virus exits the infected cell, at which time prM is cleaved to the mature M protein (Reviewed in Lindenbach and Rice, In: *Fields Virology*, Knipe and Howley, eds., Lippincott, Williams, and Wilkins, 991-1041, 2001).

Fusion protein: A protein generated by expression of a nucleic acid sequence engineered from nucleic acid sequences encoding at least a portion of two different (heterologous) proteins. To create a fusion protein, the nucleic acid sequences must be in the same reading frame and contain to internal stop codons. For example, a fusion protein includes a dengue virus E protein fused to a heterologous protein.

Immune response: A response of a cell of the immune system, such as a B-cell, T-cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immunogen: A compound, composition, or substance which is capable, under appropriate conditions, of stimulating an immune response, such as the production of antibodies or a T-cell response in an animal, including compositions that are injected or absorbed into an animal. As used herein, as "immunogenic composition" is a composition comprising an immunogen (such as a flavivirus E protein).

Immunize: To render a subject protected from an infectious disease, such as by vaccination.

Isolated: An "isolated" or "purified" biological component (such as a nucleic acid, peptide, protein, protein complex, or particle) has been substantially separated, produced apart from, or purified away from other biological components in the cell of the organism in which the component naturally occurs, that is, other chromosomal and extrachromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

P28: A region of the complement protein C3d that functions as a molecular adjuvant. In some embodiments, the amino acid sequence of the P28 region is KFLTTAKDKNR-WEDPGKQLYNVEATSYA (SEQ ID NO: 21). Fusion of the P28 region of C3d has previously been shown to enhance immunogenicity of the fused antigen (see, for example, Dunn et al., *Virology J* 7:95, 2010).

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compositions, such as one or more influenza vaccines, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Premembrane protein (prM protein): A flavivirus structural protein. The prM protein is an approximately 25 kDa protein that is the intracellular precursor for the membrane (M) protein. prM is believed to stabilize the E protein during transport of the immature virion to the cell surface. When the virus exits the infected cell, the prM protein is cleaved to the mature M protein, which is part of the viral envelope (Reviewed in Lindenbach and Rice, In: *Fields Virology*, Knipe and Howley, eds., Lippincott, Williams, and Wilkins, 991-1041, 2001).

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In some embodiments herein, the promoter is a CMV promoter.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid, protein or virus is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. The term recombinant includes nucleic acids, proteins and viruses that have been altered solely by addition, substitution, or deletion of a portion of a natural nucleic acid molecule, protein or virus.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.* 6:119-129, 1994.

The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Subject: Living multi-cellular vertebrate organisms, a category that includes both human and non-human mammals, such as non-human primates.

Tetravalent dengue virus vaccine: Refers to a dengue virus vaccine having four different antigenic determinants, such as four different E proteins (for example, one universal E protein from each of DENV-1, DENV-2, DENV-3 and DENV-4). In some embodiments, the tetravalent dengue virus vaccine is a composition comprising DENV-1, DENV-2, DENV-3 and DENV-4 VLPs, or nucleic acid molecules encoding DENV-1, DENV-2, DENV-3 and DENV-4 VLPs.

Therapeutically effective amount: A quantity of a specified agent sufficient to achieve a desired effect in a subject being treated with that agent. For example, this may be the amount of a dengue virus vaccine useful for eliciting an immune response in a subject and/or for preventing infection by dengue virus. Ideally, in the context of the present disclosure, a therapeutically effective amount of a flavivirus vaccine is an amount sufficient to increase resistance to, prevent, ameliorate, and/or treat infection caused by the flavivirus in a subject without causing a substantial cytotoxic effect in the subject. The effective amount of a flavivirus vaccine useful for increasing resistance to, preventing, ameliorating, and/or treating infection in a subject will be dependent on, for example, the subject being treated, the manner of administration of the therapeutic composition and other factors.

Transformed: A "transformed" cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Vaccine: A preparation of immunogenic material capable of stimulating an immune response, administered for the prevention, amelioration, or treatment of infectious or other types of disease. The immunogenic material may include attenuated or killed microorganisms (such as bacteria or viruses), or antigenic proteins, peptides or DNA derived from them. An attenuated vaccine is a virulent organism that has been modified to produce a less virulent form, but nevertheless retains the ability to elicit antibodies and cell-mediated immunity against the virulent form. A killed vaccine is a previously virulent microorganism that has been killed with chemicals or heat, but elicits antibodies against the virulent microorganism. Vaccines may elicit both prophylactic (preventative) and therapeutic responses. Methods of administration vary according to the vaccine, but may include inoculation, ingestion, inhalation or other forms of administration. Vaccines may be administered with an adjuvant to boost the immune response.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of inserted gene or genes. In some embodiments of the present disclosure, the vector encodes a flavivirus E protein. In some embodiments, the vector is the pTR600 expression vector (U.S. Patent Application Publication No. 2002/0106798; Ross et al., *Nat. Immunol.* 1(2):102-103, 2000; Green et al., Vaccine 20:242-248, 2001).

Virus-like particle (VLP): Virus particles made up of one of more viral structural proteins, but lacking the viral genome. Because VLPs lack a viral genome, they are non-infectious. In addition, VLPs can often be produced by heterologous expression and can be easily purified. As described herein, flavivirus VLPs can be produced by transfection of host cells with a plasmid encoding the prM and E proteins. After incubation of the transfected cells for an appropriate time to allow for protein expression (such as approximately 48 hours), VLPs can be isolated from cell culture supernatants.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Disclosed herein are computationally optimized broadly reactive ("universal" or "consensus") dengue virus E polypeptide sequences for DENV-1, DENV-2, DENV-3 and DENV-4. Also disclosed are dengue virus E protein fragments (such as the E protein ectodomain or DIII domain) fused to the molecular adjuvant P28. The disclosed nucleic acid and polypeptide sequences can be used as vaccines for eliciting an immune response against dengue virus.

Provided herein are isolated nucleic acid molecules that include a nucleotide sequence encoding a dengue virus E protein, or a fragment thereof. In some embodiments, the dengue virus E protein is a universal dengue virus E protein for DENV-1, DENV-2, DENV-3 or DENV-4. In other embodiments, the dengue virus E protein fragment comprises the E protein ectodomain of the universal dengue virus E protein for DENV-1, DENV-2, DENV-3 or DENV-4. In other embodiments, the E protein fragment is the DIII domain of DENV-1, DENV-2, DENV-3 or DENV-4. In some embodiments, the nucleic acid molecules further encode a dengue virus prM protein. Further provided are vectors comprising the nucleic acid molecules, and isolated cells comprising the vectors.

In particular non-limiting embodiments, provided is an isolated nucleic acid molecule comprising a nucleotide sequence encoding a dengue virus E protein or a fragment thereof, wherein: (a) the nucleotide sequence encoding the dengue virus E protein is at least 95%, at least 96%, at least 97%, at least 98%, or at least 99% identical to SEQ ID NO: 1, SEQ ID NO: 3, SEQ ID NO: 5 or SEQ ID NO: 7; (b) the fragment comprises the E protein ectodomain and the nucleotide sequence encoding the E protein ectodomain is at least 95%, at least 96%, at least 97%, at least 98%, or at least 99% identical to nucleotides 1-1194 of SEQ ID NO: 1, nucleotides 1-1194 of SEQ ID NO: 3, nucleotides 1-1188 of SEQ ID NO: 5, or nucleotides 1-1194 of SEQ ID NO: 7; or (c) the fragment comprises the DIII domain of the E protein and the nucleotide sequence encoding the DIII domain is at least 95%, at least 96%, at least 97%, at least 98%, or at least 99% identical to SEQ ID NO: 13, SEQ ID NO: 15, SEQ ID NO: 17, or SEQ ID NO: 19.

In some examples, the nucleotide sequence encoding the dengue virus E protein that is at least 95%, at least 96%, at least 97%, at least 98%, or at least 99% identical to SEQ ID NO: 1, SEQ ID NO: 3, SEQ ID NO: 5 or SEQ ID NO: 7 lacks the start codon (nucleotides 1-3 of each sequence), encoding a N-terminal methionine. In some examples, the nucleotide sequence encoding the dengue virus E protein is at least 99% identical to nucleotides 4-1488 of SEQ ID NO: 1, nucleotides 4-1488 of SEQ ID NO: 3, nucleotides 4-1491 of SEQ ID NO: 5, or nucleotides 4-1488 of SEQ ID NO: 7.

In some examples, the nucleotide sequence encoding the E protein comprises, or consists of, SEQ ID NO: 1, SEQ ID NO: 3, SEQ ID NO: 5 or SEQ ID NO: 7. In other examples, the nucleotide sequence encoding the E protein comprises, or consists of, nucleotides 4-1488 of SEQ ID NO: 1, nucleotides 4-1488 of SEQ ID NO: 3, nucleotides 4-1491 of SEQ ID NO: 5, or nucleotides 4-1488 of SEQ ID NO: 7.

In some examples, the nucleotide sequence encoding the E protein ectodomain that is at least 95%, at least 96%, at least 97%, at least 98%, or at least 99% identical to nucleotides 1-1194 of SEQ ID NO: 1, nucleotides 1-1194 of SEQ ID NO: 3, nucleotides 1-1188 of SEQ ID NO: 5, or nucleotides 1-1194 of SEQ ID NO: 7 lacks the start codon (nucleotides 1-3 of each sequence), encoding a N-terminal methionine. In some examples, the nucleotide sequence encoding the E protein ectodomain is at least 99% identical to nucleotides 4-1194 of SEQ ID NO: 1, nucleotides 4-1194 of SEQ ID NO: 3, nucleotides 4-1188 of SEQ ID NO: 5, or nucleotides 4-1194 of SEQ ID NO: 7.

In some examples, the nucleotide sequence encoding the E protein ectodomain comprises or consists of nucleotides 1-1194 of SEQ ID NO: 1, nucleotides 1-1194 of SEQ ID NO: 3, nucleotides 1-1188 of SEQ ID NO: 5, or nucleotides 1-1194 of SEQ ID NO: 7. In other examples, the nucleotide sequence encoding the E protein ectodomain is at least 99% identical to nucleotides 4-1194 of SEQ ID NO: 1, nucleotides 4-1194 of SEQ ID NO: 3, nucleotides 4-1188 of SEQ ID NO: 5, or nucleotides 4-1194 of SEQ ID NO: 7.

In some examples, the nucleotide sequence encoding the DIII domain comprises, or consists of, SEQ ID NO: 13, SEQ ID NO: 15, SEQ ID NO: 17 or SEQ ID NO: 19.

In particular examples in which the nucleotide sequence encodes an E protein fragment (such as the ectodomain or DIII domain), the isolated nucleic acid further comprising a nucleotide sequence encoding the P28 region of complement protein C3d. In one example, the amino acid sequence of the P28 region of complement protein C3d comprises KFLT-TAKDKNRWEDPGKQLYNVEATSYA (SEQ ID NO: 21). In some cases, the nucleic acid includes multiple copies of the P28 coding sequence, such as two, three, four or five copies.

Further provided are vectors, such as eukaryotic expression vectors, comprising the isolated nucleic acid molecules disclosed herein. Suitable vectors are well known in the art. In some examples, the vector is the pTR600 expression vector (U.S. Patent Application Publication No. 2002/0106798, herein incorporated by reference; Ross et al., *Nat. Immunol.* 1(2):102-103, 2000; Green et al., Vaccine 20:242-248, 2001).

In some examples, the vector further includes a promoter operably linked to the nucleotide sequence encoding the E protein, or fragment thereof. In particular examples, the promoter is a cytomegalovirus (CMV) promoter.

In some examples, the vector further includes a nucleic acid sequence encoding a dengue virus prM protein.

Also provided are dengue virus E proteins, or fragments thereof, produced by transfecting a host cell with a vector as described herein, under conditions sufficient to allow for expression of the protein. Further provided are isolated cells comprising a vector described herein.

Further provided herein are isolated dengue virus E proteins, or fragments thereof. In some embodiments, the dengue virus E protein is a universal dengue virus E protein derived from DENV-1, DENV-2, DENV-3 or DENV-4. In other embodiments, the E protein fragment is the E protein ectodomain of the universal dengue virus E protein of DENV-1, DENV-2, DENV-3 or DENV-4. In yet other embodiments, the E protein fragment is the DIII domain of DENV-1, DENV-2, DENV-3 or DENV-4. Further provided are VLPs comprising a universal dengue virus E protein, or fragment thereof. In some cases, the VLP further includes a dengue virus prM protein. Also provided are fusion proteins comprising a universal dengue virus E protein, or fragment thereof.

In particular non-limiting embodiments, provided is an isolated dengue virus E protein, or fragment thereof, wherein: (a) the amino acid sequence of the E protein is at least 95%, at least 96%, at least 97%, at least 98% or at least 99% identical to SEQ ID NO: 2, SEQ ID NO: 4, SEQ ID NO: 6 or SEQ ID NO: 8; (b) the fragment comprises the E protein ectodomain and the amino acid sequence of the ectodomain is at least 95%, at least 96%, at least 97%, at least 98% or at least 99% identical to amino acids 1-398 of SEQ ID NO: 2, amino acids 1-398 of SEQ ID NO: 4, amino acids 1-396 of SEQ ID NO: 6 or amino acids 1-398 of SEQ ID NO: 8; or (c) the fragment comprises the DIII domain of the E protein and the amino acid sequence of the DIII domain is at least 95%, at least 96%, at least 97%, at least 98% or at least 99% identical to SEQ ID NO: 14, SEQ ID NO: 16, SEQ ID NO: 18 or SEQ ID NO: 20.

In some examples, the amino acid sequence of the E protein that is at least 95%, at least 96%, at least 97%, at least 98% or at least 99% identical to SEQ ID NO: 2, SEQ ID NO: 4, SEQ ID NO: 6 or SEQ ID NO: 8 lacks the N-terminal methionine residue. In some examples, the amino acid sequence of the E protein is at least 99% identical to amino acids 2-495 of SEQ ID NO: 2, amino acids 2-495 of SEQ ID NO: 4, amino acids 2-493 of SEQ ID NO: 6 or amino acids 2-495 of SEQ ID NO: 8.

In some examples, the amino acid sequence of the E protein comprises, or consists of, SEQ ID NO: 2, SEQ ID NO: 4, SEQ ID NO: 6 or SEQ ID NO: 8. In other examples, the amino acid sequence of the E protein comprises, or consists of, amino acids 2-495 of SEQ ID NO: 2, amino acids 2-495 of SEQ ID NO: 4, amino acids 2-493 of SEQ ID NO: 6 or amino acids 2-495 of SEQ ID NO: 8.

In some examples, the amino acid sequence of the ectodomain that is at least 99% identical to amino acids 1-398 of SEQ ID NO: 2, amino acids 1-398 of SEQ ID NO: 4, amino acids 1-396 of SEQ ID NO: 6 or amino acids 1-398 of SEQ ID NO: 8 lacks the N-terminal methionine residue. In some examples, the amino acid sequence of the ectodomain is at least 99% identical to amino acids 2-398 of SEQ ID NO: 2, amino acids 2-398 of SEQ ID NO: 4, amino acids 2-396 of SEQ ID NO: 6 or amino acids 2-398 of SEQ ID NO: 8.

In some examples, the amino acid sequence of the E protein ectodomain comprises, or consists of, amino acids 1-398 of SEQ ID NO: 2, amino acids 1-398 of SEQ ID NO: 4, amino acids 1-396 of SEQ ID NO: 6 or amino acids 1-398 of SEQ ID NO: 8. In other examples, the amino acid sequence of the ectodomain comprises, or consists of, amino acids 2-398 of SEQ ID NO: 2, amino acids 2-398 of SEQ ID NO: 4, amino acids 2-396 of SEQ ID NO: 6 or amino acids 2-398 of SEQ ID NO: 8

In some examples, the amino acid sequence of the DIII domain comprises, or consists of, SEQ ID NO: 14, SEQ ID NO: 16, SEQ ID NO: 18 or SEQ ID NO: 20.

Also provided are fusion proteins comprising a dengue virus E protein or E protein fragment as disclosed herein.

Also provided are dengue virus-like particles (VLPs) comprising a dengue virus E protein, or a dengue virus E protein ectodomain fragment, as disclosed herein. In some embodiments, the dengue VLP further comprises a dengue virus prM protein. Further provided is a dengue VLP comprising a dengue virus E protein, or a dengue virus E protein ectodomain fragment, produced by transfecting a host cell with a vector encoding a dengue virus prM protein and the E protein or E protein ectodomain fragment, under conditions sufficient to allow for expression of the prM and E proteins.

Compositions comprising the disclosed nucleic acid molecules, vectors, dengue virus E proteins (and fragments thereof), VLPs and fusion proteins are also provided by the present disclosure. In some embodiments, the composition is a tetravalent composition comprising DENV-1, DENV-2, DENV-3 and DENV-4 universal E proteins, or nucleic acid molecules encoding the universal E proteins.

In some embodiments, the composition comprises a pharmaceutically acceptable carrier. In some embodiments, the composition comprises an adjuvant. For example, the adjuvant can be alum, Freund's complete adjuvant, a biological adjuvant or immunostimulatory oligonucleotides (such as CpG oligonucleotides).

Further provided are methods of eliciting an immune response by administration of a nucleic acid molecule, vector, dengue virus E protein (or fragment thereof), VLP or fusion protein as disclosed herein. In some embodiments, the method includes administration of a single type of dengue virus E protein, or fragment thereof. In other embodiments, the method includes administration of a tetravalent composition including E proteins (or fragments thereof) derived from all four dengue virus serotypes.

Also provided are methods of immunizing a subject against dengue virus infection by administration of a VLP, or a DNA molecule encoding a VLP, as disclosed herein. In some embodiments, the method of immunization includes administration of a composition including a VLP from a single serotype of dengue virus (i.e. a DENV-1, DENV-2, DENV-3 or DENV-4 VLP). In other embodiments, the method of immunization includes administration of VLPs from all four dengue virus serotypes (i.e., DENV-1, DENV-2, DENV-3 and DENV-4 VLPs). In some examples of the method, the composition further comprises an adjuvant. In some examples, the composition is administered intramuscularly. In other examples, the composition is administered intradermally. In some examples, the composition is administered by gene gun.

In some embodiments of the methods of eliciting an immune response or immunizing a subject, the subject is administered about 1 to about 25 μg of the VLPs containing the universal E protein, or fragment thereof. In particular examples, the subject is administered about 5 to about 20 μg of the VLPs, or about 10 to about 15 μg of the VLPs. In one specific non-limiting example, the subject is administered about 10 μg of the VLPs. However, one of skill in the art is capable of determining a therapeutically effective amount (for example an amount that provides protection against dengue virus infection) of VLPs to administer to a subject.

In one embodiment, provided is a tetravalent dengue virus vaccine comprising: (1) a vector encoding a dengue virus E protein at least 95%, at least 96%, at least 97%, at least 98% or at least 99% identical to SEQ ID NO: 2, or a dengue virus E protein fragment at least 95%, at least 96%, at least 97%, at least 98% or at least 99% identical to amino acids 1-398 of SEQ ID NO: 2; (2) a vector encoding a dengue virus E protein at least 95%, at least 96%, at least 97%, at least 98% or at least 99% identical to SEQ ID NO: 4, or a dengue virus E protein fragment at least 95%, at least 96%, at least 97%, at least 98% or at least 99% identical to amino acids 1-398 of SEQ ID NO: 4; (3) a vector encoding a dengue virus E protein at least 95%, at least 96%, at least 97%, at least 98% or at least 99% identical to SEQ ID NO: 6, or a dengue virus E protein fragment at least 95%, at least 96%, at least 97%, at least 98% or at least 99% identical to amino acids 1-396 of SEQ ID NO: 6; and (4) a vector encoding a dengue virus E protein at least 95%, at least 96%, at least 97%, at least 98% or at least 99% identical to SEQ ID NO: 8, or a dengue virus E protein fragment at least 95%, at least 96%, at least 97%, at least 98% or at least 99% identical to amino acids 1-398 of SEQ ID NO: 8.

In another embodiment, provided is a tetravalent dengue virus vaccine comprising: (1) a vector encoding a dengue virus E protein at least 95%, at least 96%, at least 97%, at least 98% or at least 99% identical to amino acids 2-495 SEQ ID NO: 2, or a dengue virus E protein fragment at least 95%, at least 96%, at least 97%, at least 98% or at least 99% identical to amino acids 2-398 of SEQ ID NO: 2; (2) a vector encoding a dengue virus E protein at least 95%, at least 96%, at least 97%, at least 98% or at least 99% identical to amino acids 2-495 SEQ ID NO: 4, or a dengue virus E protein fragment at least 95%, at least 96%, at least 97%, at least 98% or at least 99% identical to amino acids 2-398 of SEQ ID NO: 4; (3) a vector encoding a dengue virus E protein at least 95%, at least 96%, at least 97%, at least 98% or at least 99% identical to amino acids 2-493 SEQ ID NO: 6, or a dengue virus E protein fragment at least 95%, at least 96%, at least 97%, at least 98% or at least 99% identical to amino acids 2-396 of SEQ ID NO: 6; and (4) a vector encoding a dengue virus E protein at least 95%, at least 96%, at least 97%, at least 98% or at least 99% identical to amino acids 2-495 SEQ ID NO: 8, or a dengue virus E protein fragment at least 95%, at least 96%, at least 97%, at least 98% or at least 99% identical to amino acids 2-398 of SEQ ID NO: 8.

In another embodiment, provided is a tetravalent dengue virus vaccine comprising: (1) a dengue VLP comprising a dengue virus E protein at least 95%, at least 96%, at least 97%, at least 98% or at least 99% identical to SEQ ID NO: 2, or a dengue virus E protein fragment at least 95%, at least 96%, at least 97%, at least 98% or at least 99% identical to amino acids 1-398 of SEQ ID NO: 2; (2) a dengue VLP comprising a dengue virus E protein at least 95%, at least 96%, at least 97%, at least 98% or at least 99% identical to SEQ ID NO: 4, or a dengue virus E protein fragment at least 95%, at least 96%, at least 97%, at least 98% or at least 99% identical to amino acids 1-398 of SEQ ID NO: 4; (3) a dengue VLP comprising a dengue virus E protein at least 95%, at least 96%, at least 97%, at least 98% or at least 99% identical to SEQ ID NO: 6, or a dengue virus E protein fragment at least 95%, at least 96%, at least 97%, at least 98% or at least 99% identical to amino acids 1-396 of SEQ ID NO: 6; and (4) a dengue VLP comprising a dengue virus E protein at least 95%, at least 96%, at least 97%, at least 98% or at least 99% identical to SEQ ID NO: 8, or a dengue virus E protein fragment at least 95%, at least 96%, at least 97%, at least 98% or at least 99% identical to amino acids 1-398 of SEQ ID NO: 8.

In yet another embodiment, provided is a tetravalent dengue virus vaccine comprising: (1) a dengue VLP comprising a dengue virus E protein at least 95%, at least 96%, at least 97%, at least 98% or at least 99% identical to amino acids 2-495 SEQ ID NO: 2, or a dengue virus E protein fragment at least 95%, at least 96%, at least 97%, at least 98% or at least 99% identical to amino acids 2-398 of SEQ ID NO: 2; (2) a dengue VLP comprising a dengue virus E protein at least 95%, at least 96%, at least 97%, at least 98% or at least 99% identical to amino acids 2-495 SEQ ID NO: 4, or a dengue virus E protein fragment at least 95%, at least 96%, at least 97%, at least 98% or at least 99% identical to amino acids 2-398 of SEQ ID NO: 4; (3) a dengue VLP comprising a dengue virus E protein at least 95%, at least 96%, at least 97%, at least 98% or at least 99% identical to amino acids 2-493 SEQ ID NO: 6, or a dengue virus E protein fragment at least 95%, at least 96%, at least 97%, at least 98% or at least 99% identical to amino acids 2-396 of SEQ ID NO: 6; and (4) a dengue VLP comprising a dengue virus E protein at least 95%, at least 96%, at least 97%, at least 98% or at least 99% identical to amino acids 2-495 SEQ ID NO: 8, or a dengue virus E protein fragment at least 95%, at least 96%, at least 97%, at least 98% or at least 99% identical to amino acids 2-398 of SEQ ID NO: 8.

Further provided is a method of eliciting an immune response against dengue virus in a subject by administering to the subject a tetravalent dengue virus vaccine as described herein, thereby eliciting an immune response against dengue virus in the subject. Also provided is a method of immunizing a subject against dengue virus by administering to the subject a tetravalent dengue virus vaccine as described herein, thereby immunization the subject against dengue virus.

IV. Dengue Virus Consensus E Proteins and VLPs Thereof

Dengue fever (DF), the most prevalent arthropod-borne viral illness in humans, is caused by DENV. Two-thirds of the world's population is located in DENV endemic regions. The four serotypes of DENV are transmitted to humans primarily by the *Aedes aegypti* mosquito. DENV is a member of the *Flaviviridae* family and is related to the viruses that cause yellow fever and the Japanese, St. Louis, and West Nile encephalitides. Infection by DENV causes a spectrum of clinical diseases ranging from acute debilitating, self-limited febrile illness (DF) to a life threatening hemorrhagic/capillary leak syndrome (DHF/DSS). No approved antiviral treatment or vaccine is currently in use. DENV causes 25-100 million cases of DF and 250,000 cases of DHF per year, with 2.5 billion people at risk for infection.

Design of an efficacious DENV vaccine will not only elicit protective immunity, but will also prevent enhanced illness due to antibody-dependent enhancement (ADE). The present disclosure combines two approaches to overcome these challenges: (1) the use of consensus E proteins minimizes the degree of sequence dissimilarity between vaccine immunogens and circulating virus strains by generating artificial sequences based on the most common amino acid in each position in an alignment; and (2) the use of VLPs will elicit broadly reactive anti-dengue immunity by retaining linear and conformational epitopes in E proteins that induce both humoral and cellular immune responses. Purified VLPs can be administered directly as a vaccine, or nucleic acid molecules (such as vectors) encoding the consensus E proteins that comprise the VLP can be administered. The use of the non-infectious VLP elicits broadly reactive immunity without the dangers of a live-attenuated viral vaccine. These vaccines generate multi-serotype responses capable of withstanding the generation of escape mutants. In addition, VLPs offer the opportunity for entry of particles into professional antigen presenting cells (APCs) like dendritic cells and macrophages.

A. Use of Virus-Like Particle-Based Vaccines

Virus-like particles (VLPs), noninfectious virions composed of structural proteins but lacking a viral genome, can be produced in various cell expression systems from DNA plasmids encoding selected viral structural proteins. A major advantage of a VLP-based vaccine compared to live-attenuated virus is that a VLP expresses multiple viral epitopes that stimulate a diverse set of immune responses without many of the potential deleterious effects of a live-attenuated virus. VLPs have the potential for activating both the endogenous and exogenous antigen pathways leading to the presentation of viral peptides by major histocompatibility complex (MHC) class I and class II molecules. These multi-epitope vaccines are more likely than their single component counterparts to generate a broad-based immune response capable of recognizing and inactivating diverse DENV strains. Moreover, one vaccine expressing dengue virus VLPs may be more cost efficient than co-inoculation of multiple single gene vaccines for future phase I clinical trials.

An additional advantage of VLPs compared to single recombinant protein vaccines is the ability of VLPs to bind and enter cells using appropriate surface receptors. After infection, viral proteins can be processed and presented on MHC class I molecules, thereby promoting presentation to T-cells by APCs. In addition, cell-free VLPs bound with antibodies can be taken up by phagocytic cells via Fc receptors, thus increasing MHC class II presentation.

Antigens expressed in their native conformational form can elicit more effective antibody responses than proteins in their non-native forms. Many neutralizing antibodies directed against viruses are elicited against conformational epitopes that are present only in the native form of envelopes, and some are exposed only after binding to receptors during entry. Many recombinant protein-based vaccines elicit high titer antibodies against the envelope (Env) glycoproteins, however, these antibodies often only neutralize the homologous virus and not other viral isolates. In contrast, Env presented as a native trimer conformation more effectively elicits neutralizing antibodies. Particle-based vaccines, containing native forms of Env, in addition to other viral antigens, have the potential to induce strong humoral and cell-mediated responses to multiple viral proteins.

B. Use of Consensus DENY E Protein Sequences

Centralized gene strategies based on computer models (consensus, ancestor, and center of the tree) have been used to construct vaccine immunogens that can produce enhanced immunity against viruses that display a high level of diversity, such as HIV-1. Consensus HIV-1 envelopes have been shown to incorporate into VLPs and to mediate infection, indicating the biological relevance (structure/function) of these artificial sequences. Immunogenicity studies indicate that these consensus sequence immunogens can broaden vaccine cellular and humoral immune responses to recognize diverse HIV-1 strains. Consensus sequences minimize the degree of sequence dissimilarity between vaccine immunogens and circulating virus strains by creating artificial sequences based on the most common amino acid in each position in an alignment. Consensus sequences are the most representative of current circulating viral populations. Combining several consensus sequences has advantages for covering as many epitopes as possible within a diverse immunogen like the DENV E protein.

The use of consensus E immunogens, expressed on the surface of a VLP in a native form, elicits broadly reactive anti-DENV immunity. This immunogen design retains linear epitopes in E that are critical for the induction of cellular immunity, as well as the conformational epitopes found in the E oligomer to elicit broad humoral responses to viral isolates. In addition, the use of consensus envelope sequences eliminates the need to select the correct strain to use as the vaccine immunogen from among diverse isolates within a serotype. The use of consensus E protein can be used to elicit immune responses to combat exposure to strains from multiple DENV genotypes.

C. Design of VLPs

In contrast to current attenuated DENV E vaccine approaches, the strategies disclosed herein for the development, manufacture, and administration of DENV vaccines do not require the use of any live dengue virus. Thus, problems associated with the availability, safety, and handling of infectious DENV are no longer an issue. VLP-based vaccines are an innovative technology for efficient, safe, low-cost vaccines for viral diseases, including DENV.

Recombinant VLP vaccines preserve native, conformational antigenic epitopes of DENV proteins in the context of highly immunogenic, noninfectious structures. The robust immunogenicity of VLP vaccines elicits immune responses seroprotection with low doses of E antigen, which reduces the vaccine's side effects and reactogenicity. Recombinant VLP vaccines are intrinsically safer than vaccines derived from live attenuated or inactivated whole virus vaccines, avoiding the safety risks associated with the presence of infectious virus in the process of vaccine development and production.

V. Dengue VLPs and Administration Thereof

Dengue VLPs comprising a consensus E protein (such as the E protein having the amino acid sequence set forth as any one of SEQ ID NOs: 2, 4, 6 or 8), or fragment thereof, are provided herein. The dengue VLPs are made up of the prM and E proteins. The production of dengue VLPs has been described in the art and is within the abilities of one of ordinary skill in the art. As described herein, dengue virus VLPs can be produced by transfection of host cells with a plasmid encoding the prM and E proteins. After incubation of the transfected cells for an appropriate time to allow for protein expression, VLPs can be isolated from cell culture supernatants according to standard procedures.

Also provided herein are nucleic acid molecules encoding dengue VLPs. Thus, in some embodiments, provided are nucleic acid molecules encoding the prM and E proteins, wherein the E protein is a consensus E protein sequence (such as the protein encoded by the nucleic acid sequence of any one of SEQ ID NOs: 1, 3, 5 or 7), or fragment thereof.

The dengue VLPs (including nucleic acid molecules encoding dengue virus VLPs) disclosed herein can be used as dengue virus vaccines to elicit a protective immune response against any dengue virus group, subtype or Glade, including any emerging viruses.

Dengue VLPs, or compositions thereof, can be administered to a subject by any of the routes normally used for introducing recombinant virus or nucleic acid molecules into a subject. Methods of administration include, but are not limited to, intradermal, intramuscular, intraperitoneal, parenteral, intravenous, subcutaneous, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, and tablets of the kind previously described. Administration can be systemic or local.

Dengue VLPs (or nucleic acid molecules encoding dengue VLPs), or compositions thereof, are administered in any suitable manner, such as with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Particular methods for administering nucleic acid molecules are well known in the art. In some examples, the nucleic acid encoding the dengue VLP is administered by injection (such as intramuscular or intradermal injection) or by gene gun.

Administration can be accomplished by single or multiple doses. The dose administered to a subject in the context of the present disclosure should be sufficient to induce a beneficial therapeutic response in a subject over time, or to inhibit or prevent dengue virus infection. The dose required will vary from subject to subject depending on the species, age, weight and general condition of the subject, the severity of the infection being treated, the particular composition being used and its mode of administration. An appropriate dose can be determined by one of ordinary skill in the art using only routine experimentation.

In some embodiments, the dose of dengue VLP is about 1 to about 100 µg. In particular examples, the dose of dengue VLP is about 5, about 10, about 15, about 20, about 25, or about 50 µg.

In some embodiments, the dose of nucleic acid molecule encoding the dengue VLP is about 0.02 to about 20 µg. In particular examples, the dose of nucleic acid molecule encoding the dengue virus VLP is about 0.1, about 0.2, about 0.4, about 0.6, about 0.8, about 1.0, about 1.5, about 2.0, about 2.5, about 3.0, about 5.0 or about 10 µg.

Provided herein are pharmaceutical compositions which include a therapeutically effective amount of the dengue VLPs (or nucleic acid molecules encoding the dengue VLPs) alone or in combination with a pharmaceutically acceptable carrier. Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

The dengue VLPs (or nucleic acid molecules encoding the dengue virus VLPs) described herein can be administered alone or in combination with other therapeutic agents to enhance antigenicity. For example, the dengue virus VLPs can be administered with an adjuvant, such as Freund incomplete adjuvant or Freund's complete adjuvant.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, can be used as biological adjuvants (see, for example, Salgaller et al., 1998, *J. Surg. Oncol.* 68(2):122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host.

Although administration of VLPs containing a consensus E protein is described herein, one of skill in the art would understand that it is also possible to administer the consensus E protein itself (in the absence of a viral particle) or as a fusion protein to elicit an immune response in a subject.

The following examples are provided to illustrate certain particular features and/or embodiments. These examples should not be construed to limit the disclosure to the particular features or embodiments described.

EXAMPLES

Example 1

DENY-1 VLP Vaccine

The universal dengue virus E sequences were designed by computationally determining the common amino acid structure of each envelope gene at each position. This sequence allows for the conservation of epitopes from all strains of dengue virus from a particular group, subtype, or Glade. This allows for a sequence with high antigenic activity and high immunogenic activity that results in the elicitation of highly cross-reactive immune responses to all dengue viruses using a single sequence. The sequences are applicable to vaccine development for current and emerging dengue strains.

Disclosed herein are highly immunogenic sequences that can be used to elicit immune responses that recognize all strains of dengue virus. A wild-type dengue sequence will elicit immune responses to the homologous strain and closely evolutionarily-related strains. The universal sequence can elicit immunity from a single sequence to currently circulating strains, as well as future emerging strains of the pathogen.

Construction and Expression of DNA Vaccine Plasmids

The eukaryotic expression vector, pTR600, has been previously described (Mitchell et al., *Vaccine* 21:902-914, 2003; Green et al., *J. Virol.* 77:2046-2055, 2003) and was used for expression of the prM and E gene segments of DENV-1. A BamHI restriction endonuclease site was introduced using site directed mutagenesis immediately 5' to the TAG stop site. DNA vaccine plasmids were amplified in *Escherichia coli*, purified using anion-exchange resin columns (Qiagen, Valencia, Calif.) and stored at −20° C. in dH20. Plasmids were verified by appropriate restriction enzyme digestion and sequencing. 293T cells were transfected with 3 µg of DNA using Lipofectamine™ 2000 according to the manufacturer's instructions (Invitrogen, Carlsbad, Calif.). Cell culture supernatants were collected 48 hrs post-transfection. Approximately 1.5% of sample volume was loaded onto a 10% polyacrylamide/SDS gel. The resolved proteins were transferred onto an Immobilon PVDF membrane (Millipore, Temecula, Calif.) and incubated with a 1:5000 dilution of the dengue virus specific monoclonal antibody (mAb 8150, Chemicon, Temecula, Calif.) in PBS containing 0.05% Tween-20 and 5% nonfat dry milk. After extensive washing, bound antibodies were detected using a 1:10,000 dilution of horseradish peroxidase-conjugated goat anti-mouse antiserum, and visualized by chemiluminescence (Western Lightning™, Perkin Elmer, Waltham, Mass.).

Vaccination

Female C57BL/6 mice (n=5-8 mice per group; aged 6-8 weeks) were purchased from Harlan Sprague Dawley, (Indianapolis, Ind., USA), immunized with each DNA vaccine plasmid by gene gun (particle bombardment with 2 µg DNA coated on gold bullets) and then boosted with the same dose on weeks 3 and 6. In some cases 0.2 µg or 0.02 µg of vaccine plasmid as a dose response was administered in a mixture of vector plasmid to keep a total of 2 µg total DNA vaccine. Blood was collected from anesthetized mice via the retroorbital route on weeks 5 and 8 post vaccination, then centrifuged at 6000 rpm for 10 minutes to separate the serum. Sera were transferred to new vials and frozen at −20° C.

Enzyme-Linked Immunosorbent Assay (ELISA)

A quantitative ELISA was performed to assess anti-DIII specific IgG in serum of vaccinated mice. Individual wells of a 96 microtiter plate were coated overnight at 4° C. with DENV 1 DIII proteins produced from transfected 293T cells and then blocked (25° C. for 2 hours) with PBS supplemented with Tween-20 (0.05%) and nonfat dry milk (5%). Each serum sample was serially diluted and incubated (25° C. for 2 hours). Following serial washes with PBS Tween-20 (0.05%), samples were incubated (25° C. for 1 hour) with HRP conjugated goat anti-mouse IgG (1:5000) or one of four IgG subclasses (IgG1, IgG2a, IgG2b, or IgG3) (Southern Biotechnology, Birmingham, Ala.) diluted in PBS Tween-20 (0.05%) and nonfat dry milk (5%). Unbound antibody was removed and after additional washes samples were incubated with TMB substrate, and the colorimetric change was measured as the optical density at 405 nm using a plate reader (Biotek Powerwave XS, Winooski, Vt. USA). The OD value of the age-matched naïve sera was subtracted from the OD values of the antisera from the vaccinated mice. Results were recorded as the geometric mean titer (GMT)±the standard error of the mean (SEM).

Table 1 below shows the endpoint dilution titers of mice vaccinated with DNA encoding the dengue-1 VLP or vaccinated with purified dengue-1 VLPs. The titers ranged between 1:51200 and 1:204800. Mock vector vaccinated or unvaccinated mice did not have any antibody titer above the 1:100 cut-off.

TABLE 1

Endpoint dilution titers of vaccinated mice

| Dilution | WT VLP DNA | WT VLP | Mock Vector | Naïve |
| --- | --- | --- | --- | --- |
| 1:100 | 0.443 | 0.482 | 0.059 | 0.056 |
| 1:200 | 0.462 | 0.48 | 0.063 | 0.06 |
| 1:400 | 0.43 | 0.454 | 0.059 | 0.053 |
| 1:800 | 0.402 | 0.433 | 0.061 | 0.053 |
| 1:1600 | 0.342 | 0.388 | 0.057 | 0.054 |
| 1:3200 | 0.272 | 0.336 | 0.056 | 0.058 |
| 1:6400 | 0.196 | 0.257 | 0.063 | 0.057 |
| 1:12800 | 0.145 | 0.188 | 0.057 | 0.053 |
| 1:25600 | 0.109 | 0.138 | 0.059 | 0.058 |
| 1:51200 | 0.082 | 0.1 | 0.056 | 0.057 |
| 1:102400 | 0.068 | 0.091 | 0.06 | 0.056 |
| 1:204800 | 0.067 | 0.072 | 0.054 | 0.057 |

Example 2

Dengue serotypes 1-4 VLP Vaccine Constructs

Three different vaccine constructs (referred to as pSVP, pDIII-P28 and pEctoE-P28) were generated for each of DENV-1, DENV-2, DENV-3 and DENV-4. A schematic of each construct, and expression of the corresponding proteins, is shown in FIG. 1. The pSVP constructs encode a prM protein and a consensus ("universal") E protein. The pEctoE-P28 constructs encode a prM protein and the ectodomain of a consensus E protein. The pDIII-P28 constructs encode the DIII domain of the dengue virus E protein. The pEctoE-P28 and DIII-P28 constructs further encode four repeats of the P28 region of the complement protein C3d. The P28 region amino acid sequence is set forth herein as SEQ ID NO: 21. The consensus E protein, consensus ectodomain and DIII sequences are provided herein as SEQ ID NOs 1-8 and 13-20.

Expression of the pSVP and pEctoE-P28 constructs results in production of dengue virus-like particles (VLPs). Thus, these constructs can be used as DNA vaccines, which will result in the production of VLPs in the host following administration, or these constructs can be used to transfect cells for production and isolation of VLPs. The isolated VLPs can then be administered as a protein-based vaccine to a subject. The pDIII-P28 construct can similarly be administered as a DNA vaccine, which results in production of a DIII-P28 fusion protein. In some instances, the pDIII-P28 construct is administered in combination with a VLP vaccine (for example, a primary vaccination with pDIII-P28 and a boost with VLP).

Vaccine Constructs and Expression

The DIII region of the E gene (amino acids 586-705) was cloned downstream of the tpA leader sequence, and in some cases, P28 was also cloned in frame and directly after the 3' end of the DIII gene. An artificial BamHI site and stop codon was engineered at position 705 in the E gene to create the truncated Ecto E gene, and P28 was cloned into the Ecto E construct using the BamHI site to create the Ecto E-P28 construct. Supernatants from 293T cells transiently transfected with plasmid DNA expressing the SVP, DIII-P28, or the Ecto E-P28 proteins in the supernatants from each of the four subtypes (D1, D2, D3 and D4) of Dengue were assessed by SDS-PAGE and Western blot (FIG. 1B). Protein was detected in cell supernatants following transfection of each of the constructs.

Immunization Studies

The vaccination regimen and doses of each construct used for the immunization studies described below is shown in FIG. 2. Initial studies included vaccination of mice with the DNA constructs pSVP, pDIII-P28 and pEctoE-P28, and with the VLP vaccine SVP for each of DENV-1, DENV-2, DENV-3 and DENV-4.

Figure 3:
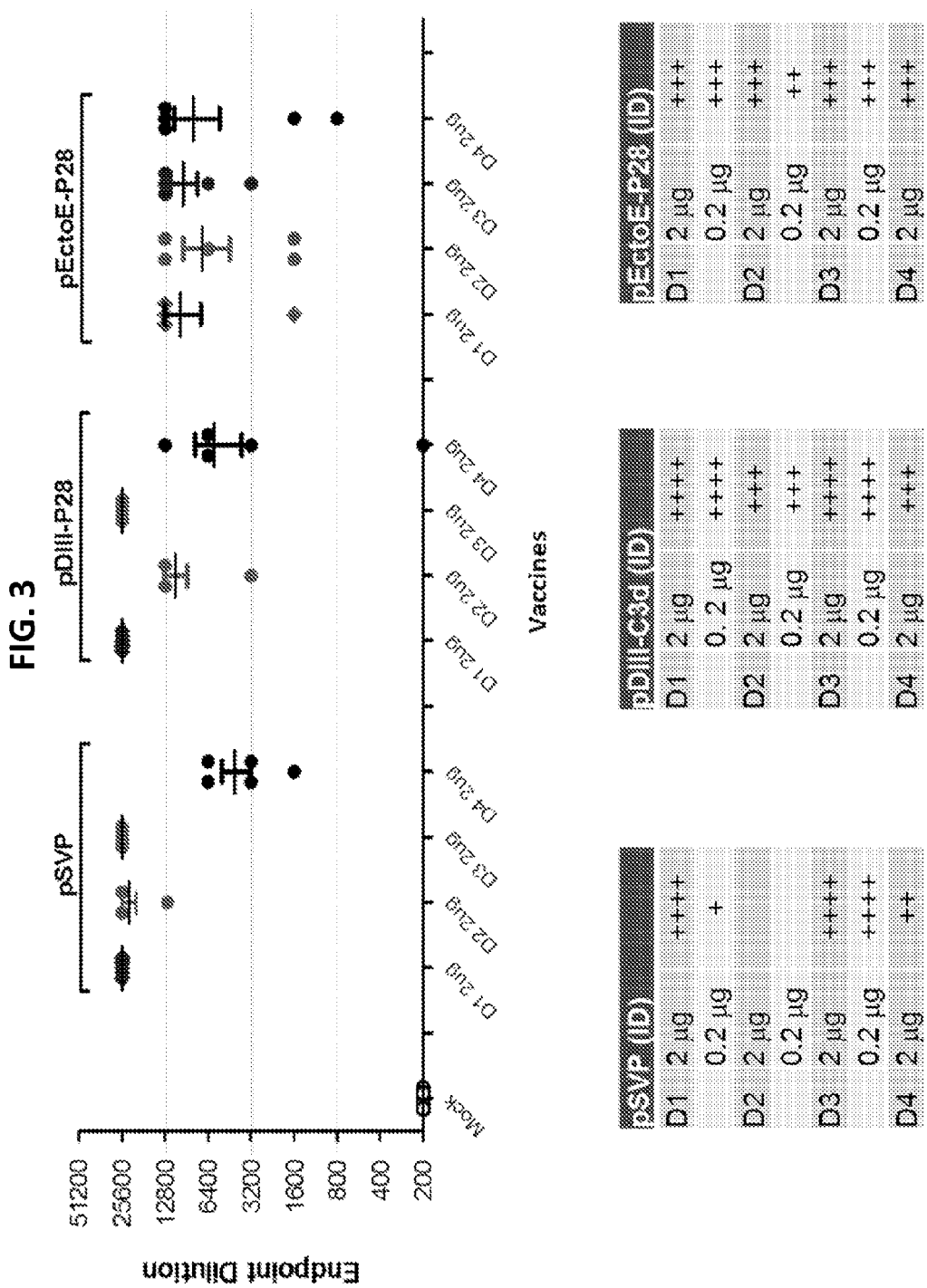

The DNA vaccine constructs were tested for the capacity to elicit dengue virus-specific antibodies following intradermal administration by gene gun. FIG. 3 shows endpoint titers following vaccination with the three DNA constructs for DENV-1, DENV-2, DENV-3 and DENV-4. As shown in FIG. 3, each of the constructs elicited DIII-specific IgG antibody following vaccination.

Figure 4:
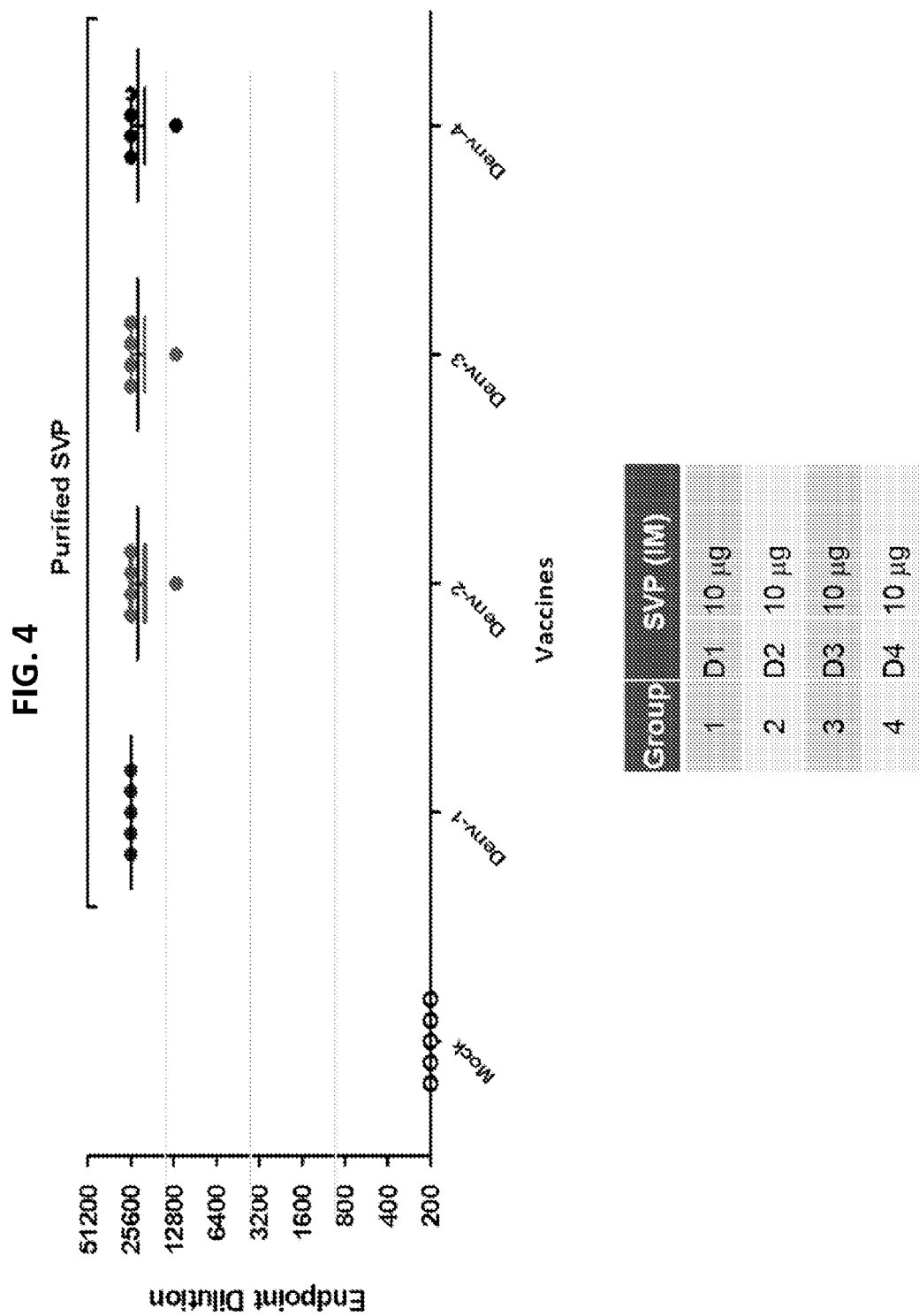
Figure 5:
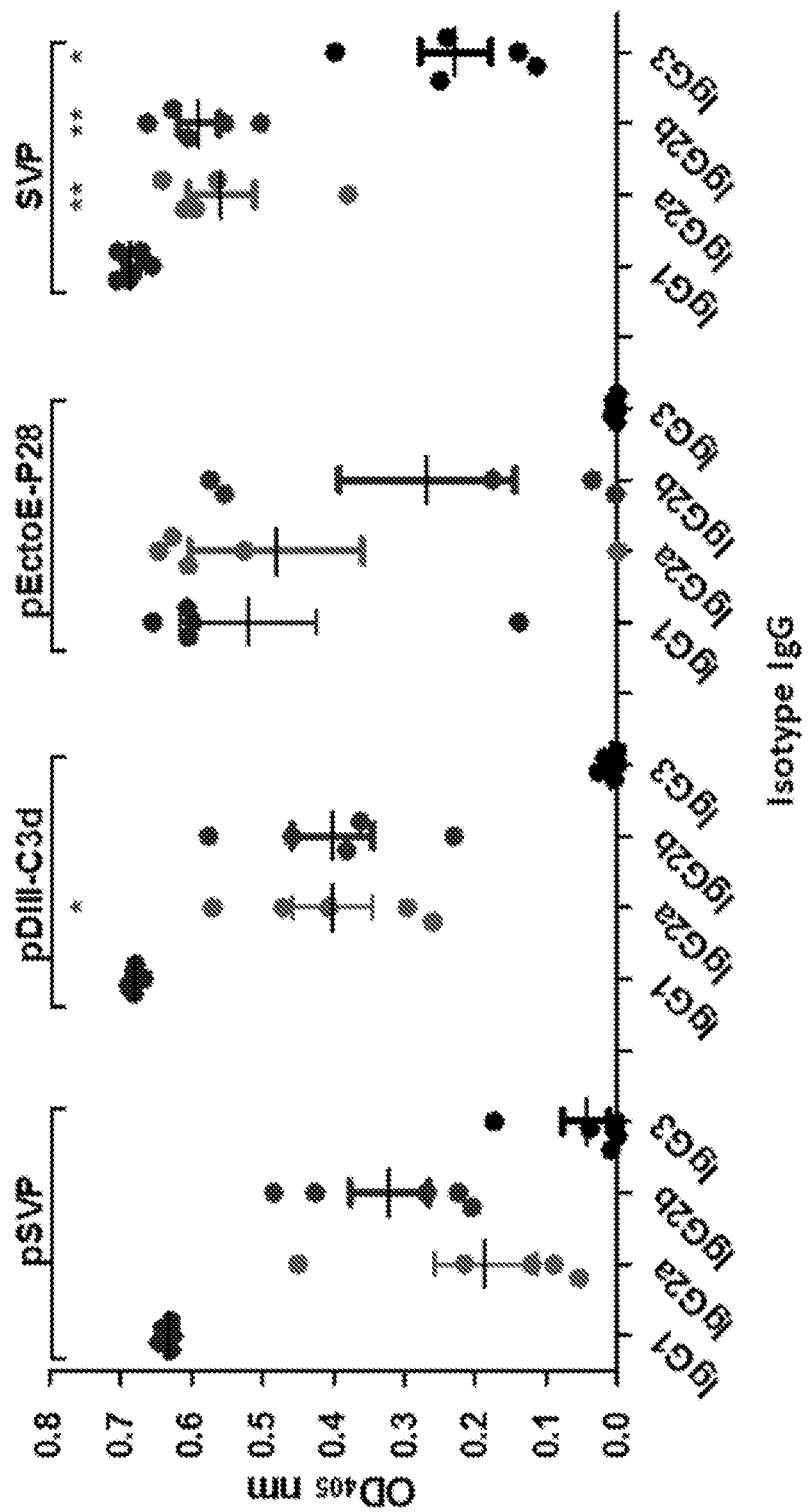

Similarly, immunization with purified SVPs was evaluated for the production of dengue virus-specific antibodies. FIG. 4 shows endpoint titers following vaccination (by intramuscular injection) with purified SVP. Total IgG titers were measured by ELISA on Dengue DIII-coated plates from mice vaccinated intramuscularly with purified SVPs on week 8. As shown in FIG. 4, each type of SVP (DENV-1, DENV-2, DENV-3 and DENV-4) was capable of eliciting dengue-specific antibodies. FIG. 5 shows the titer of IgG isotypes following vaccination with the three DNA constructs and purified tetravalent SVP.

Figure 6:
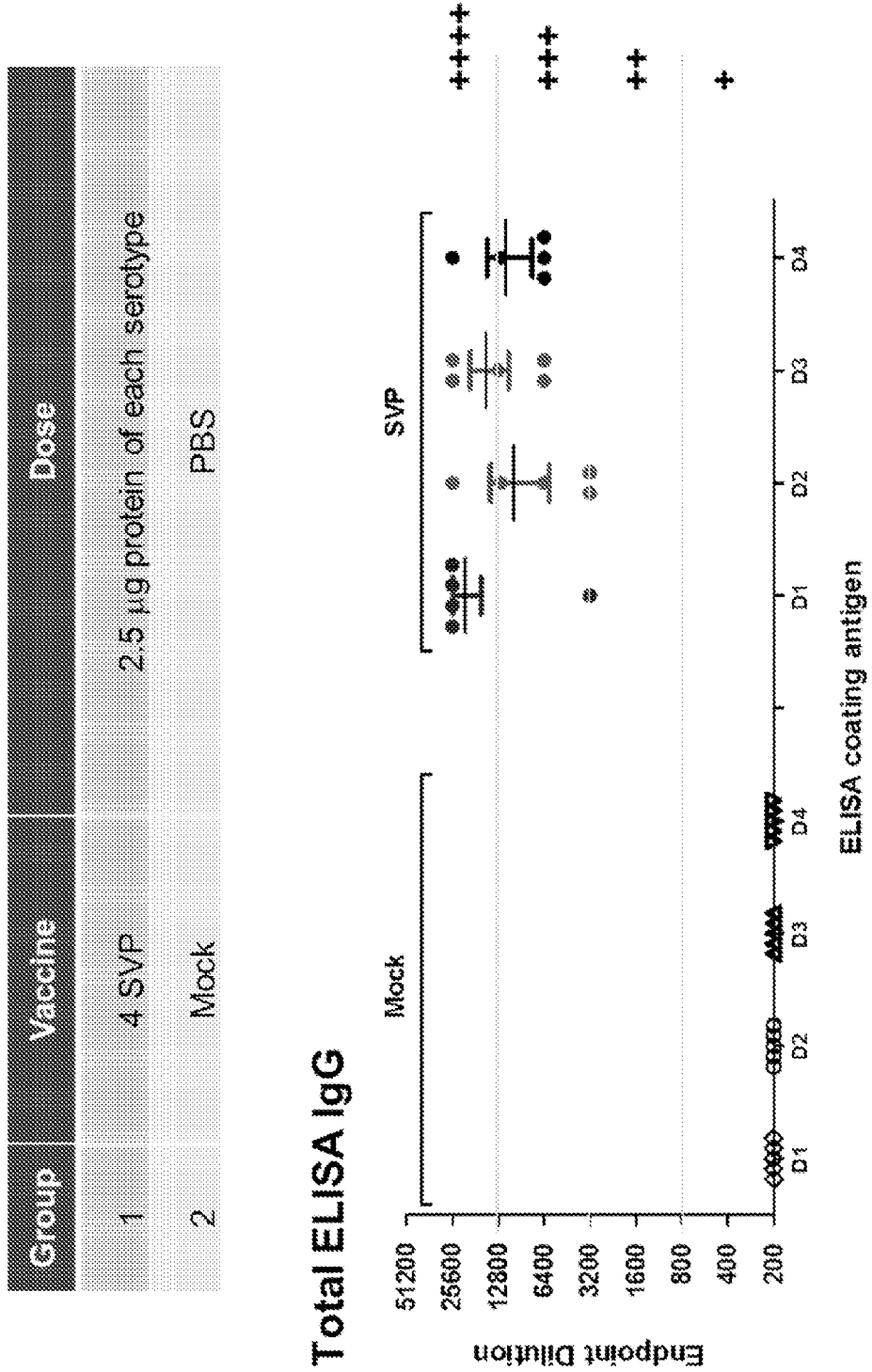
Figure 7A:
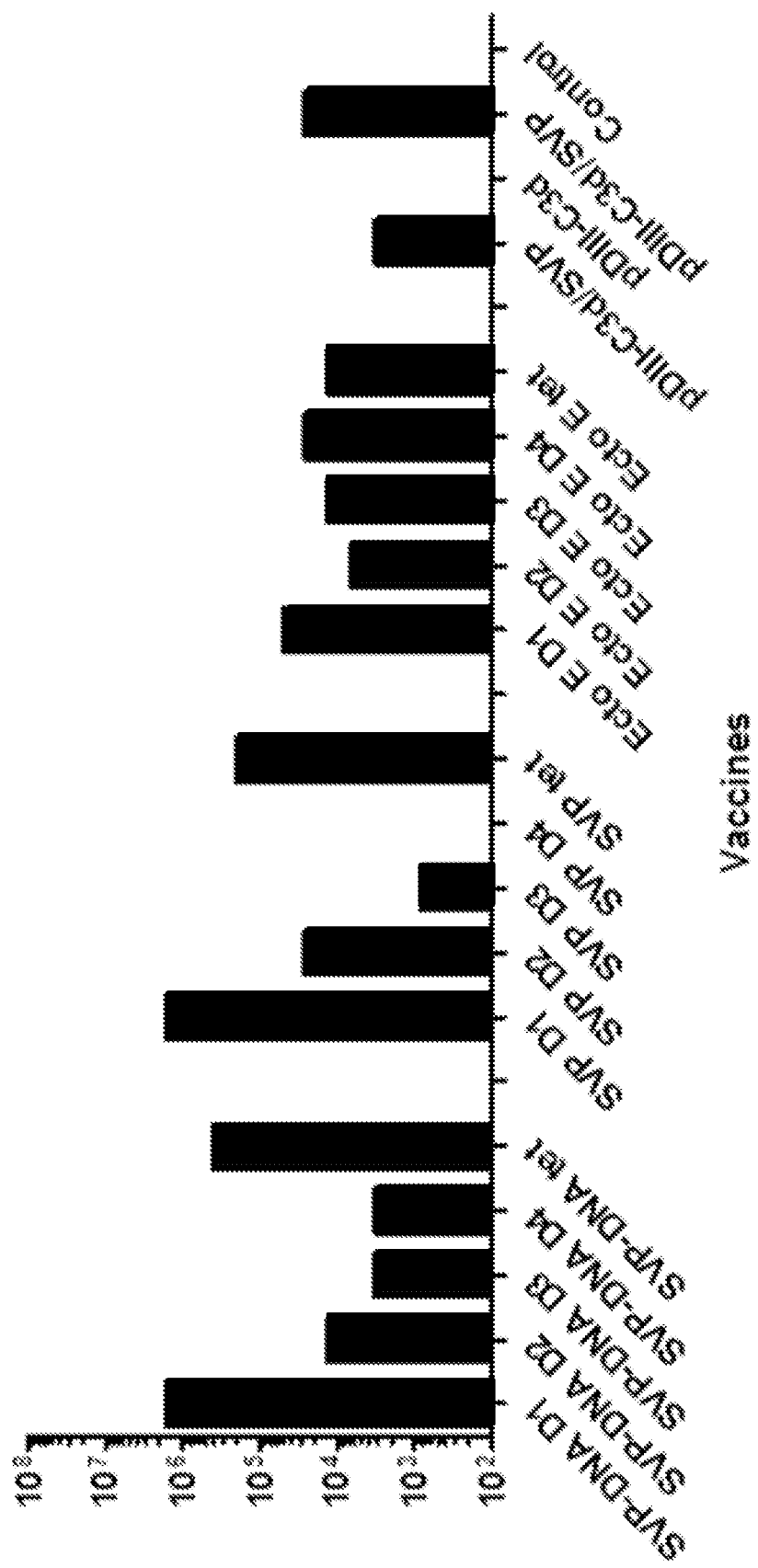

Next, a tetravalent mixture, combining SVP from each of DENV-1, DENV-2, DENV-3 and DENV-4, was tested for the ability to elicit dengue virus-specific antibodies following intramuscular injection. Total titers were measured by ELISA on Dengue DIII-coated plates (the plates were coated with DIII from either DENV-1, DENV-2, DENV-3 and DENV-4). FIG. 6 shows the endpoint titers of total IgG following vaccination with the tetravalent SVP vaccine. The tetravalent mixture elicited antibodies that recognized DIII from all four different dengue virus serotypes.

Further studies were carried out to evaluate individual cross-reactive ELISA titers against DENV-1, DENV-2, DENV-3, DENV-4 and WNV against the full length Dengue E protein. Total IgG titers were measured by ELISA on Dengue E coated plates from mice vaccinated intramuscularly on week 8. As shown in FIGS. 7A-7E, mice were vaccinated with pSVP (SVP DNA), purified SVP, or purified EctoE-P28 (Ecto E) for each dengue virus serotype, or a tetravalent mixture of either pSVP (SVP-DNA tet), SVP (SVP tet) or EctoE-P28 (Ecto E tet). Additional mice were vaccinated with pDIII-C3d alone or in combination with SVP (pDIII-C3d/SVP). Each construct elicited antibodies that recognized the corresponding E protein, and in many cases, elicited antibodies that recognized E proteins from other dengue serotypes. In addition, vaccination with the tetravalent combinations resulted in production of antibodies that recognized E proteins from all four serotypes.

It will be apparent that the precise details of the methods or compositions described may be varied or modified without departing from the spirit of the described invention. We claim all such modifications and variations that fall within the scope and spirit of the claims below.

The invention claimed is:

1. An isolated nucleic acid molecule comprising a nucleotide sequence encoding a dengue virus E protein or a fragment thereof, wherein:
 (a) the nucleotide sequence encoding the dengue virus E protein is at least 99% identical to SEQ ID NO: 1 or at least 99% identical to nucleotides 4-1488 of SEQ ID NO: 1;
 (b) the fragment comprises the E protein ectodomain and the nucleotide sequence encoding the E protein ectodomain is at least 99% identical to nucleotides 1-1194 of SEQ ID NO: 1 or at least 99% identical to nucleotides 4-1194 of SEQ ID NO: 1; or
 (c) the fragment comprises the DIII domain of the E protein and the nucleotide sequence encoding the DIII domain is at least 99% identical to SEQ ID NO: 13.

2. The isolated nucleic acid molecule of claim 1, wherein the nucleotide sequence encoding the E protein comprises SEQ ID NO: 1.

3. The isolated nucleic acid molecule of claim 1, wherein the nucleotide sequence encoding the E protein ectodomain comprises nucleotides 1-1194 of SEQ ID NO: 1.

4. The isolated nucleic acid molecule of claim 1, the fragment of (b) further comprising a nucleotide sequence encoding the P28 region of complement protein C3d.

5. The isolated nucleic acid molecule of claim 1, wherein the nucleic acid molecule comprises a nucleotide sequence encoding the E protein ectodomain or the E protein DIII domain and further comprises a nucleotide sequence encoding the P28 region of complement protein C3d.

6. The isolated nucleic acid molecule of claim 5, wherein the amino acid sequence of the P28 region of complement protein C3d comprises SEQ ID NO: 21.

7. A vector comprising the isolated nucleic acid molecule of claim 1.

8. The vector of claim 7, further comprising a nucleic acid sequence encoding a dengue virus prM protein.

9. An isolated cell comprising the vector of claim 7.

10. A composition comprising the nucleic acid molecule of claim 1 and a pharmaceutically acceptable carrier.

11. A method of eliciting an immune response against dengue virus in a subject, comprising administering to the subject the composition of claim 10, thereby eliciting an immune response against dengue virus in the subject.

* * * * *

SEQUENCE LISTING

```
<160> NUMBER OF SEQ ID NOS: 21

<210> SEQ ID NO 1
<211> LENGTH: 1488
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1)..(1488)
<223> OTHER INFORMATION: DENV-1 consensus E protein coding sequence
<220> FEATURE:
<221> NAME/KEY: misc_feature
<222> LOCATION: (1)..(1194)
<223> OTHER INFORMATION: Ecto E coding sequence

<400> SEQUENCE: 1 atg cga tgc gtg gga ata ggc aac aga gac ttc gtg gaa gga ctg tca        48
Met Arg Cys Val Gly Ile Gly Asn Arg Asp Phe Val Glu Gly Leu Ser
1               5                   10                  15 gga gca acg tgg gtg gat gtg gta ctg gag cat gga agt tgc gtc acc        96
Gly Ala Thr Trp Val Asp Val Val Leu Glu His Gly Ser Cys Val Thr
            20                  25                  30 acc atg gca aaa aat aaa cca aca ctg gac att gaa ctc ttg aag acg       144
Thr Met Ala Lys Asn Lys Pro Thr Leu Asp Ile Glu Leu Leu Lys Thr
        35                  40                  45
```

```
gag gtc aca aac cct gcc gtc ctg cgc aaa ctg tgc att gaa gct aaa      192
Glu Val Thr Asn Pro Ala Val Leu Arg Lys Leu Cys Ile Glu Ala Lys
 50                  55                  60 ata tca aac acc acc acc gat tca aga tgt cca aca caa gga gaa gcc      240
Ile Ser Asn Thr Thr Thr Asp Ser Arg Cys Pro Thr Gln Gly Glu Ala
 65                  70                  75                  80 aca ctg gtg gaa gaa caa gac gcg aac ttt gtg tgc cga cga acg ttt      288
Thr Leu Val Glu Glu Gln Asp Ala Asn Phe Val Cys Arg Arg Thr Phe
                 85                  90                  95 gtg gac aga ggc tgg ggc aat ggc tgt ggg cta ttc gga aaa ggt agc      336
Val Asp Arg Gly Trp Gly Asn Gly Cys Gly Leu Phe Gly Lys Gly Ser
            100                 105                 110 cta ata acg tgt gct aag ttt aag tgt gtg aca aaa cta gaa gga aag      384
Leu Ile Thr Cys Ala Lys Phe Lys Cys Val Thr Lys Leu Glu Gly Lys
        115                 120                 125 ata gtt caa tat gaa aac tta aaa tat tca gtg ata gtc acc gtc cac      432
Ile Val Gln Tyr Glu Asn Leu Lys Tyr Ser Val Ile Val Thr Val His
130                 135                 140 act gga gac cag cac cag gtg gga aat gag act aca gaa cat gga aca      480
Thr Gly Asp Gln His Gln Val Gly Asn Glu Thr Thr Glu His Gly Thr
145                 150                 155                 160 act gca acc ata aca cct caa gct ccc acg tcg gaa ata cag ctg acc      528
Thr Ala Thr Ile Thr Pro Gln Ala Pro Thr Ser Glu Ile Gln Leu Thr
                165                 170                 175 gac tac gga gct ctc aca ttg gat tgt tca cct aga aca ggg cta gac      576
Asp Tyr Gly Ala Leu Thr Leu Asp Cys Ser Pro Arg Thr Gly Leu Asp
            180                 185                 190 ttt aat gag atg gtg ttg ttg aca atg aaa gaa aaa tca tgg ctt gtc      624
Phe Asn Glu Met Val Leu Leu Thr Met Lys Glu Lys Ser Trp Leu Val
        195                 200                 205 cac aaa caa tgg ttt cta gac tta cca ctg cct tgg acc tcg ggg gct      672
His Lys Gln Trp Phe Leu Asp Leu Pro Leu Pro Trp Thr Ser Gly Ala
210                 215                 220 tca aca tcc caa gag act tgg aac aga caa gat ttg ctg gtc aca ttt      720
Ser Thr Ser Gln Glu Thr Trp Asn Arg Gln Asp Leu Leu Val Thr Phe
225                 230                 235                 240 aag aca gct cat gca aag aag cag gaa gta gtc gta cta gga tca caa      768
Lys Thr Ala His Ala Lys Lys Gln Glu Val Val Val Leu Gly Ser Gln
                245                 250                 255 gaa gga gca atg cac act gcg ttg act gga gcg aca gaa atc caa acg      816
Glu Gly Ala Met His Thr Ala Leu Thr Gly Ala Thr Glu Ile Gln Thr
            260                 265                 270 tca gga acg aca aca att ttt gca gga cac ctg aaa tgc aga cta aaa      864
Ser Gly Thr Thr Thr Ile Phe Ala Gly His Leu Lys Cys Arg Leu Lys
        275                 280                 285 atg gat aaa ctg act tta aaa ggg atg tca tat gtg atg tgc aca ggc      912
Met Asp Lys Leu Thr Leu Lys Gly Met Ser Tyr Val Met Cys Thr Gly
290                 295                 300 tca ttc aag tta gag aaa gaa gtg gct gag acc cag cat gga act gtt      960
Ser Phe Lys Leu Glu Lys Glu Val Ala Glu Thr Gln His Gly Thr Val
305                 310                 315                 320 cta gtg cag gtt aaa tac gaa gga aca gat gca cca tgc aag atc ccc     1008
Leu Val Gln Val Lys Tyr Glu Gly Thr Asp Ala Pro Cys Lys Ile Pro
                325                 330                 335 ttt tcg acc caa gat gag aaa gga gta acc cag aat ggg aga ttg ata     1056
Phe Ser Thr Gln Asp Glu Lys Gly Val Thr Gln Asn Gly Arg Leu Ile
            340                 345                 350 aca gcc aac ccc ata gtc act gac aaa gaa aaa cca gtc aac att gag     1104
Thr Ala Asn Pro Ile Val Thr Asp Lys Glu Lys Pro Val Asn Ile Glu
```

```
                   355                 360                 365
gca aaa cca cct ttt ggt gag agc tac atc gtg gta gga gca ggt gaa       1152
Ala Glu Pro Pro Phe Gly Glu Ser Tyr Ile Val Val Gly Ala Gly Glu
    370                 375                 380 aaa gct ttg aaa cta agc tgg ttc aag aaa gga agc agc ata ggg aaa       1200
Lys Ala Leu Lys Leu Ser Trp Phe Lys Lys Gly Ser Ser Ile Gly Lys
385                 390                 395                 400 atg ttt gaa gca act gcc cga gga gca cga agg atg gcc atc ctg gga       1248
Met Phe Glu Ala Thr Ala Arg Gly Ala Arg Arg Met Ala Ile Leu Gly
                405                 410                 415 gac acc gca tgg gac ttc ggt tct ata gga ggt gtt ttc acg tct gtg       1296
Asp Thr Ala Trp Asp Phe Gly Ser Ile Gly Gly Val Phe Thr Ser Val
            420                 425                 430 gga aaa ctg gta cac cag att ttt gga act gca tat gga gtt ttg ttc       1344
Gly Lys Leu Val His Gln Ile Phe Gly Thr Ala Tyr Gly Val Leu Phe
        435                 440                 445 agc ggt gtt tct tgg acc atg aaa ata gga ata ggg att ctg ctg aca       1392
Ser Gly Val Ser Trp Thr Met Lys Ile Gly Ile Gly Ile Leu Leu Thr
    450                 455                 460 tgg cta gga tta aat tca agg agc acg tcc ctt tcg atg acg tgc atc       1440
Trp Leu Gly Leu Asn Ser Arg Ser Thr Ser Leu Ser Met Thr Cys Ile
465                 470                 475                 480 gca gtt ggc atg gtc aca ctg tac cta gga gtc atg gtt cag gcg tga       1488
Ala Val Gly Met Val Thr Leu Tyr Leu Gly Val Met Val Gln Ala
                485                 490                 495

<210> SEQ ID NO 2
<211> LENGTH: 495
<212> TYPE: PRT
<213> ORGANISM: Artificial Sequence
<220> FEATURE:
<223> OTHER INFORMATION: Synthetic Construct

<400> SEQUENCE: 2

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asn Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Ala Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Thr Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190
```

-continued

```
Phe Asn Glu Met Val Leu Leu Thr Met Lys Glu Lys Ser Trp Leu Val
            195                 200                 205
His Lys Gln Trp Phe Leu Asp Leu Pro Leu Pro Trp Thr Ser Gly Ala
        210                 215                 220
Ser Thr Ser Gln Glu Thr Trp Asn Arg Gln Asp Leu Leu Val Thr Phe
225                 230                 235                 240
Lys Thr Ala His Ala Lys Lys Gln Glu Val Val Val Leu Gly Ser Gln
                245                 250                 255
Glu Gly Ala Met His Thr Ala Leu Thr Gly Ala Thr Glu Ile Gln Thr
            260                 265                 270
Ser Gly Thr Thr Thr Ile Phe Ala Gly His Leu Lys Cys Arg Leu Lys
        275                 280                 285
Met Asp Lys Leu Thr Leu Lys Gly Met Ser Tyr Val Met Cys Thr Gly
290                 295                 300
Ser Phe Lys Leu Glu Lys Glu Val Ala Glu Thr Gln His Gly Thr Val
305                 310                 315                 320
Leu Val Gln Val Lys Tyr Glu Gly Thr Asp Ala Pro Cys Lys Ile Pro
                325                 330                 335
Phe Ser Thr Gln Asp Glu Lys Gly Val Thr Gln Asn Gly Arg Leu Ile
            340                 345                 350
Thr Ala Asn Pro Ile Val Thr Asp Lys Glu Lys Pro Val Asn Ile Glu
        355                 360                 365
Ala Glu Pro Pro Phe Gly Glu Ser Tyr Ile Val Val Gly Ala Gly Glu
    370                 375                 380
Lys Ala Leu Lys Leu Ser Trp Phe Lys Lys Gly Ser Ser Ile Gly Lys
385                 390                 395                 400
Met Phe Glu Ala Thr Ala Arg Gly Ala Arg Arg Met Ala Ile Leu Gly
                405                 410                 415
Asp Thr Ala Trp Asp Phe Gly Ser Ile Gly Gly Val Phe Thr Ser Val
            420                 425                 430
Gly Lys Leu Val His Gln Ile Phe Gly Thr Ala Tyr Gly Val Leu Phe
        435                 440                 445
Ser Gly Val Ser Trp Thr Met Lys Ile Gly Ile Gly Ile Leu Leu Thr
    450                 455                 460
Trp Leu Gly Leu Asn Ser Arg Ser Thr Ser Leu Ser Met Thr Cys Ile
465                 470                 475                 480
Ala Val Gly Met Val Thr Leu Tyr Leu Gly Val Met Val Gln Ala
                485                 490                 495
```

<210> SEQ ID NO 3
<211> LENGTH: 1488
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1)..(1488)
<223> OTHER INFORMATION: DENV-2 consensus E protein coding sequence
<220> FEATURE:
<221> NAME/KEY: misc_feature
<222> LOCATION: (1)..(1194)
<223> OTHER INFORMATION: Ecto E coding sequence

<400> SEQUENCE: 3

```
atg cgt tgc ata gga ata tca aat aga gac ttt gta gaa ggg gtt tca       48
Met Arg Cys Ile Gly Ile Ser Asn Arg Asp Phe Val Glu Gly Val Ser
1               5                   10                  15
```

| | | | |
|---|---|---|---|
| gga gga agc tgg gtt gac ata gtc tta gaa cat gga agc tgt gtg acg<br>Gly Gly Ser Trp Val Asp Ile Val Leu Glu His Gly Ser Cys Val Thr<br>20              25              30 | | | 96 |
| acg atg gca aaa aac aaa cca aca ttg gat ttt gaa ctg ata aaa aca<br>Thr Met Ala Lys Asn Lys Pro Thr Leu Asp Phe Glu Leu Ile Lys Thr<br>    35              40              45 | | | 144 |
| gaa gcc aaa caa cct gcc act cta agg aag tac tgt ata gaa gca aag<br>Glu Ala Lys Gln Pro Ala Thr Leu Arg Lys Tyr Cys Ile Glu Ala Lys<br>50              55              60 | | | 192 |
| ctg acc aac aca aca aca gaa tct cgc tgc cca aca caa ggg gaa ccc<br>Leu Thr Asn Thr Thr Thr Glu Ser Arg Cys Pro Thr Gln Gly Glu Pro<br>65              70              75              80 | | | 240 |
| agc cta aat gaa gag cag gac aaa agg ttc gtc tgc aaa cac tcc atg<br>Ser Leu Asn Glu Glu Gln Asp Lys Arg Phe Val Cys Lys His Ser Met<br>            85              90              95 | | | 288 |
| gta gac aga gga tgg gga aat gga tgt gga tta ttt gga aaa gga ggc<br>Val Asp Arg Gly Trp Gly Asn Gly Cys Gly Leu Phe Gly Lys Gly Gly<br>        100             105             110 | | | 336 |
| att gtg acc tgt gct atg ttc aca tgc aaa aag aac atg gaa gga aaa<br>Ile Val Thr Cys Ala Met Phe Thr Cys Lys Lys Asn Met Glu Gly Lys<br>    115             120             125 | | | 384 |
| atc gtg caa cca gaa aac ttg gaa tac acc atc gtg ata aca cct cac<br>Ile Val Gln Pro Glu Asn Leu Glu Tyr Thr Ile Val Ile Thr Pro His<br>130             135             140 | | | 432 |
| tca ggg gaa gag cat gca gtc gga aat gac aca gga aaa cat ggc aag<br>Ser Gly Glu Glu His Ala Val Gly Asn Asp Thr Gly Lys His Gly Lys<br>145             150             155             160 | | | 480 |
| gaa atc aaa ata aca cca cag agt tcc atc aca gaa gca gaa ctg aca<br>Glu Ile Lys Ile Thr Pro Gln Ser Ser Ile Thr Glu Ala Glu Leu Thr<br>            165             170             175 | | | 528 |
| ggc tat ggc act gtc acg atg gag tgc tct ccg aga acg ggc ctc gac<br>Gly Tyr Gly Thr Val Thr Met Glu Cys Ser Pro Arg Thr Gly Leu Asp<br>        180             185             190 | | | 576 |
| ttc aat gag atg gtg ttg ctg caa atg gaa aac aaa gct tgg ctg gtg<br>Phe Asn Glu Met Val Leu Leu Gln Met Glu Asn Lys Ala Trp Leu Val<br>    195             200             205 | | | 624 |
| cac agg caa tgg ttc cta gac ctg ccg tta cca tgg ctg ccc gga gcg<br>His Arg Gln Trp Phe Leu Asp Leu Pro Leu Pro Trp Leu Pro Gly Ala<br>210             215             220 | | | 672 |
| gac aca caa gga tca aat tgg ata cag aaa gag aca ttg gtc act ttc<br>Asp Thr Gln Gly Ser Asn Trp Ile Gln Lys Glu Thr Leu Val Thr Phe<br>225             230             235             240 | | | 720 |
| aaa aat ccc cat gcg aag aaa cag gat gtt gtt gtt tta gga tcc caa<br>Lys Asn Pro His Ala Lys Lys Gln Asp Val Val Val Leu Gly Ser Gln<br>            245             250             255 | | | 768 |
| gaa ggg gcc atg cac aca gca ctc aca ggg gcc aca gaa atc cag atg<br>Glu Gly Ala Met His Thr Ala Leu Thr Gly Ala Thr Glu Ile Gln Met<br>        260             265             270 | | | 816 |
| tca tca gga aac tta ctg ttc aca gga cat ctc aag tgc agg ctg aga<br>Ser Ser Gly Asn Leu Leu Phe Thr Gly His Leu Lys Cys Arg Leu Arg<br>    275             280             285 | | | 864 |
| atg gac aaa cta cag ctc aaa gga atg tca tac tcc atg tgc aca gga<br>Met Asp Lys Leu Gln Leu Lys Gly Met Ser Tyr Ser Met Cys Thr Gly<br>290             295             300 | | | 912 |
| aag ttt aaa gtt gtg aag gaa ata gca gaa aca caa cat gga aca ata<br>Lys Phe Lys Val Val Lys Glu Ile Ala Glu Thr Gln His Gly Thr Ile<br>305             310             315             320 | | | 960 |
| gtt atc aga gta caa tat gaa ggg gac ggc tct cca tgt aag atc cct<br>Val Ile Arg Val Gln Tyr Glu Gly Asp Gly Ser Pro Cys Lys Ile Pro | | | 1008 |

```
                  325                 330                 335
ttt gag ata atg gat ttg gaa aaa aga cat gtc tta ggt cgc ctg atc    1056
Phe Glu Ile Met Asp Leu Glu Lys Arg His Val Leu Gly Arg Leu Ile
                340                 345                 350 aca gtc aac cca att gtg aca gaa aaa gac agc cca gtc aac ata gaa    1104
Thr Val Asn Pro Ile Val Thr Glu Lys Asp Ser Pro Val Asn Ile Glu
            355                 360                 365 gca gaa cct cca ttc gga gac agc tac atc atc ata gga gta gag ccg    1152
Ala Glu Pro Pro Phe Gly Asp Ser Tyr Ile Ile Ile Gly Val Glu Pro
        370                 375                 380 gga caa ctg aag ctc aac tgg ttt aag aaa gga agt tct atc ggc caa    1200
Gly Gln Leu Lys Leu Asn Trp Phe Lys Lys Gly Ser Ser Ile Gly Gln
385                 390                 395                 400 atg ttt gag aca aca atg aga gga gcg aag aga atg gcc att tta ggt    1248
Met Phe Glu Thr Thr Met Arg Gly Ala Lys Arg Met Ala Ile Leu Gly
                405                 410                 415 gac aca gcc tgg gat ttt gga tcc ctg gga gga gtg ttc aca tct ata    1296
Asp Thr Ala Trp Asp Phe Gly Ser Leu Gly Gly Val Phe Thr Ser Ile
            420                 425                 430 gga aaa gct ctc cac caa gtt ttt gga gca atc tat ggg gct gcc ttc    1344
Gly Lys Ala Leu His Gln Val Phe Gly Ala Ile Tyr Gly Ala Ala Phe
        435                 440                 445 agt ggg gtc tca tgg act atg aaa atc ctc ata gga gtc atc atc aca    1392
Ser Gly Val Ser Trp Thr Met Lys Ile Leu Ile Gly Val Ile Ile Thr
450                 455                 460 tgg ata gga atg aac tca cgc agc acc tca ctg tct gtg tca cta gta    1440
Trp Ile Gly Met Asn Ser Arg Ser Thr Ser Leu Ser Val Ser Leu Val
                470                 475                 480
465 tta gtg gga atc gtg aca ctg tac ttg gga gtt atg gtg cag gcc taa    1488
Leu Val Gly Ile Val Thr Leu Tyr Leu Gly Val Met Val Gln Ala
            485                 490                 495

<210> SEQ ID NO 4
<211> LENGTH: 495
<212> TYPE: PRT
<213> ORGANISM: Artificial Sequence
<220> FEATURE:
<223> OTHER INFORMATION: Synthetic Construct

<400> SEQUENCE: 4

Met Arg Cys Ile Gly Ile Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
                85                  90                  95

Val Asp Arg Gly Trp Gly Asn Gly Cys Gly Leu Phe Gly Lys Gly Gly
            100                 105                 110

Ile Val Thr Cys Ala Met Phe Thr Cys Lys Lys Asn Met Glu Gly Lys
        115                 120                 125

Ile Val Gln Pro Glu Asn Leu Glu Tyr Thr Ile Val Ile Thr Pro His
    130                 135                 140
```

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
        195                 200                 205

His Arg Gln Trp Phe Leu Asp Leu Pro Leu Pro Trp Leu Pro Gly Ala
    210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
        275                 280                 285

Met Asp Lys Leu Gln Leu Lys Gly Met Ser Tyr Ser Met Cys Thr Gly
    290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
        355                 360                 365

Ala Glu Pro Pro Phe Gly Asp Ser Tyr Ile Ile Ile Gly Val Glu Pro
    370                 375                 380

Gly Gln Leu Lys Leu Asn Trp Phe Lys Lys Gly Ser Ser Ile Gly Gln
385                 390                 395                 400

Met Phe Glu Thr Thr Met Arg Gly Ala Lys Arg Met Ala Ile Leu Gly
                405                 410                 415

Asp Thr Ala Trp Asp Phe Gly Ser Leu Gly Gly Val Phe Thr Ser Ile
            420                 425                 430

Gly Lys Ala Leu His Gln Val Phe Gly Ala Ile Tyr Gly Ala Ala Phe
        435                 440                 445

Ser Gly Val Ser Trp Thr Met Lys Ile Leu Ile Gly Val Ile Ile Thr
    450                 455                 460

Trp Ile Gly Met Asn Ser Arg Ser Thr Ser Leu Ser Val Ser Leu Val
465                 470                 475                 480

Leu Val Gly Ile Val Thr Leu Tyr Leu Gly Val Met Val Gln Ala
                485                 490                 495

<210> SEQ ID NO 5
<211> LENGTH: 1491
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1)..(1491)
<223> OTHER INFORMATION: DENV-3 consensus E protein coding sequence
<220> FEATURE:
<221> NAME/KEY: misc_feature
<222> LOCATION: (1)..(1188)
<223> OTHER INFORMATION: Ecto E coding sequence

<400> SEQUENCE: 5

| | | | | | | | | | | | | | | | | |
|---|---|---|---|---|---|---|---|---|---|---|---|---|---|---|---|---|
| atg | aga | tgc | gtg | gga | gta | gga | aac | aga | gat | ttt | gtg | gaa | ggc | cta | tca | 48 |
| Met | Arg | Cys | Val | Gly | Val | Gly | Asn | Arg | Asp | Phe | Val | Glu | Gly | Leu | Ser | |
| 1 | | | | 5 | | | | | 10 | | | | | 15 | | |

| gga | gct | acg | tgg | gtt | gac | gtg | gtg | ctc | gag | cac | ggt | ggg | tgt | gtg | act | 96 |
|---|---|---|---|---|---|---|---|---|---|---|---|---|---|---|---|---|
| Gly | Ala | Thr | Trp | Val | Asp | Val | Val | Leu | Glu | His | Gly | Gly | Cys | Val | Thr | |
| | | 20 | | | | | 25 | | | | | 30 | | | | |

| acc | atg | gct | aag | aac | aag | ccc | acg | ctg | gac | ata | gag | ctt | cag | aag | acc | 144 |
|---|---|---|---|---|---|---|---|---|---|---|---|---|---|---|---|---|
| Thr | Met | Ala | Lys | Asn | Lys | Pro | Thr | Leu | Asp | Ile | Glu | Leu | Gln | Lys | Thr | |
| | | | 35 | | | | | 40 | | | | | 45 | | | |

| gag | gcc | acc | caa | ctg | gcg | acc | cta | agg | aag | cta | tgc | att | gag | gga | aaa | 192 |
|---|---|---|---|---|---|---|---|---|---|---|---|---|---|---|---|---|
| Glu | Ala | Thr | Gln | Leu | Ala | Thr | Leu | Arg | Lys | Leu | Cys | Ile | Glu | Gly | Lys | |
| 50 | | | | | 55 | | | | | 60 | | | | | | |

| att | acc | aac | ata | aca | acc | gac | tca | agg | tgt | ccc | acc | caa | ggg | gaa | gcg | 240 |
|---|---|---|---|---|---|---|---|---|---|---|---|---|---|---|---|---|
| Ile | Thr | Asn | Ile | Thr | Thr | Asp | Ser | Arg | Cys | Pro | Thr | Gln | Gly | Glu | Ala | |
| 65 | | | | 70 | | | | | 75 | | | | | 80 | | |

| att | tta | cct | gag | gag | cag | gac | cag | aac | tac | gtg | tgt | aag | cac | aca | tac | 288 |
|---|---|---|---|---|---|---|---|---|---|---|---|---|---|---|---|---|
| Ile | Leu | Pro | Glu | Glu | Gln | Asp | Gln | Asn | Tyr | Val | Cys | Lys | His | Thr | Tyr | |
| | | | | 85 | | | | | 90 | | | | | 95 | | |

| gtg | gac | aga | ggc | tgg | gga | aac | ggt | tgt | ggt | ttg | ttt | ggc | aag | gga | agc | 336 |
|---|---|---|---|---|---|---|---|---|---|---|---|---|---|---|---|---|
| Val | Asp | Arg | Gly | Trp | Gly | Asn | Gly | Cys | Gly | Leu | Phe | Gly | Lys | Gly | Ser | |
| | | | 100 | | | | | 105 | | | | | 110 | | | |

| ttg | gta | aca | tgc | gcg | aaa | ttt | caa | tgt | cta | gaa | cca | ata | gag | gga | aaa | 384 |
|---|---|---|---|---|---|---|---|---|---|---|---|---|---|---|---|---|
| Leu | Val | Thr | Cys | Ala | Lys | Phe | Gln | Cys | Leu | Glu | Pro | Ile | Glu | Gly | Lys | |
| | | 115 | | | | | 120 | | | | | 125 | | | | |

| gtg | gtg | caa | cat | gag | aac | ctc | aaa | tac | acc | gtc | atc | atc | aca | gtg | cac | 432 |
|---|---|---|---|---|---|---|---|---|---|---|---|---|---|---|---|---|
| Val | Val | Gln | His | Glu | Asn | Leu | Lys | Tyr | Thr | Val | Ile | Ile | Thr | Val | His | |
| 130 | | | | | 135 | | | | | 140 | | | | | | |

| aca | gga | gac | caa | cac | cag | gtg | gga | aat | gaa | acg | cag | gga | gtc | acg | gct | 480 |
|---|---|---|---|---|---|---|---|---|---|---|---|---|---|---|---|---|
| Thr | Gly | Asp | Gln | His | Gln | Val | Gly | Asn | Glu | Thr | Gln | Gly | Val | Thr | Ala | |
| 145 | | | | 150 | | | | | 155 | | | | | 160 | | |

| gag | ata | aca | ccc | cag | gca | tca | acc | gct | gaa | gcc | atc | tta | cct | gaa | tat | 528 |
|---|---|---|---|---|---|---|---|---|---|---|---|---|---|---|---|---|
| Glu | Ile | Thr | Pro | Gln | Ala | Ser | Thr | Ala | Glu | Ala | Ile | Leu | Pro | Glu | Tyr | |
| | | | | 165 | | | | | 170 | | | | | 175 | | |

| gga | acc | ctt | ggg | cta | gaa | tgc | tca | cca | cgg | aca | ggt | ttg | gat | ttc | aat | 576 |
|---|---|---|---|---|---|---|---|---|---|---|---|---|---|---|---|---|
| Gly | Thr | Leu | Gly | Leu | Glu | Cys | Ser | Pro | Arg | Thr | Gly | Leu | Asp | Phe | Asn | |
| | | | 180 | | | | | 185 | | | | | 190 | | | |

| gaa | atg | atc | tta | cta | aca | atg | aag | aac | aaa | gca | tgg | atg | gta | cat | aga | 624 |
|---|---|---|---|---|---|---|---|---|---|---|---|---|---|---|---|---|
| Glu | Met | Ile | Leu | Leu | Thr | Met | Lys | Asn | Lys | Ala | Trp | Met | Val | His | Arg | |
| | | 195 | | | | | 200 | | | | | 205 | | | | |

| caa | tgg | ttc | ttt | gac | cta | cct | cta | cca | tgg | aca | tca | gga | gct | aca | aca | 672 |
|---|---|---|---|---|---|---|---|---|---|---|---|---|---|---|---|---|
| Gln | Trp | Phe | Phe | Asp | Leu | Pro | Leu | Pro | Trp | Thr | Ser | Gly | Ala | Thr | Thr | |
| 210 | | | | | 215 | | | | | 220 | | | | | | |

| gaa | aca | cca | acc | tgg | aac | agg | aaa | gag | ctt | ctt | gtg | aca | ttc | aaa | aac | 720 |
|---|---|---|---|---|---|---|---|---|---|---|---|---|---|---|---|---|
| Glu | Thr | Pro | Thr | Trp | Asn | Arg | Lys | Glu | Leu | Leu | Val | Thr | Phe | Lys | Asn | |
| 225 | | | | 230 | | | | | 235 | | | | | 240 | | |

| gca | cat | gca | aaa | aaa | caa | gaa | gta | gtt | gtc | ctt | gga | tcg | caa | gag | gga | 768 |
|---|---|---|---|---|---|---|---|---|---|---|---|---|---|---|---|---|
| Ala | His | Ala | Lys | Lys | Gln | Glu | Val | Val | Val | Leu | Gly | Ser | Gln | Glu | Gly | |
| | | | | 245 | | | | | 250 | | | | | 255 | | |

| gca | atg | cac | aca | gca | ctg | aca | gga | gcc | aca | gag | atc | caa | aac | tca | gga | 816 |
|---|---|---|---|---|---|---|---|---|---|---|---|---|---|---|---|---|
| Ala | Met | His | Thr | Ala | Leu | Thr | Gly | Ala | Thr | Glu | Ile | Gln | Asn | Ser | Gly | |
| | | | 260 | | | | | 265 | | | | | 270 | | | |

| ggc | aca | agt | att | ttt | gcg | ggg | cac | tta | aaa | tgt | aga | ctt | aag | atg | gac | 864 |
|---|---|---|---|---|---|---|---|---|---|---|---|---|---|---|---|---|
| Gly | Thr | Ser | Ile | Phe | Ala | Gly | His | Leu | Lys | Cys | Arg | Leu | Lys | Met | Asp | |
| | | 275 | | | | | 280 | | | | | 285 | | | | |

| aaa | ttg | gaa | ctc | aag | ggg | atg | agc | tat | gca | atg | tgc | tcg | aat | acc | ttt | 912 |
|---|---|---|---|---|---|---|---|---|---|---|---|---|---|---|---|---|
| Lys | Leu | Glu | Leu | Lys | Gly | Met | Ser | Tyr | Ala | Met | Cys | Ser | Asn | Thr | Phe | |

```
                 290                 295                 300
gtg ttg aag aaa gaa gtc tcc gaa acg cag cat ggg aca ata ctc att    960
Val Leu Lys Lys Glu Val Ser Glu Thr Gln His Gly Thr Ile Leu Ile
305                 310                 315                 320 aag gtt gag tac aaa ggg gaa gat gca cct tgc aag att cct ttc tcc   1008
Lys Val Glu Tyr Lys Gly Glu Asp Ala Pro Cys Lys Ile Pro Phe Ser
                325                 330                 335 aca gag gat gga caa ggg aaa gct cac aat ggc aga ctg atc aca gcc   1056
Thr Glu Asp Gly Gln Gly Lys Ala His Asn Gly Arg Leu Ile Thr Ala
            340                 345                 350 aac cca gtg gtg acc aag aag gag gag cct gtc aac att gag gct gaa   1104
Asn Pro Val Val Thr Lys Lys Glu Glu Pro Val Asn Ile Glu Ala Glu
        355                 360                 365 cct cct ttt ggg gaa agt aac ata gtg att gga att gga gac aaa gcc   1152
Pro Pro Phe Gly Glu Ser Asn Ile Val Ile Gly Ile Gly Asp Lys Ala
    370                 375                 380 ttg aaa atc aac tgg tac aag aag gga agc tcg att ggg aag atg ttc   1200
Leu Lys Ile Asn Trp Tyr Lys Lys Gly Ser Ser Ile Gly Lys Met Phe
385                 390                 395                 400 gag gcc act gcc aga ggt gca agg cgc atg gcc atc ttg gga gac aca   1248
Glu Ala Thr Ala Arg Gly Ala Arg Arg Met Ala Ile Leu Gly Asp Thr
                405                 410                 415 gcc tgg gac ttt gga tca gtg ggt ggt gtt cta aac tca tta gga aaa   1296
Ala Trp Asp Phe Gly Ser Val Gly Gly Val Leu Asn Ser Leu Gly Lys
            420                 425                 430 atg gtg cac caa ata ttc gga agt gct tac aca gcc cta ttt agt gga   1344
Met Val His Gln Ile Phe Gly Ser Ala Tyr Thr Ala Leu Phe Ser Gly
        435                 440                 445 gtc tct tgg ata atg aaa att gga ata ggt gtc ctc tta acc tgg ata   1392
Val Ser Trp Ile Met Lys Ile Gly Ile Gly Val Leu Leu Thr Trp Ile
    450                 455                 460 ggg ttg aat tca aaa aac act tcc atg tca ttt tca tgc att gcg ata   1440
Gly Leu Asn Ser Lys Asn Thr Ser Met Ser Phe Ser Cys Ile Ala Ile
465                 470                 475                 480 gga atc att aca ctc tat ctg gga gcc gtg gtg caa gct taa tct aga   1488
Gly Ile Ile Thr Leu Tyr Leu Gly Ala Val Val Gln Ala     Ser Arg
                485                 490                     495 taa                                                               1491

<210> SEQ ID NO 6
<211> LENGTH: 493
<212> TYPE: PRT
<213> ORGANISM: Artificial Sequence
<220> FEATURE:
<223> OTHER INFORMATION: Synthetic Construct

<400> SEQUENCE: 6

Met Arg Cys Val Gly Val Gly Asn Arg Asp Phe Val Glu Gly Leu Ser
1               5                   10                  15

Gly Ala Thr Trp Val Asp Val Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Ile Leu Pro Glu Glu Gln Asp Gln Asn Tyr Val Cys Lys His Thr Tyr
                85                  90                  95
```

```
Val Asp Arg Gly Trp Gly Asn Gly Cys Gly Leu Phe Gly Lys Gly Ser
                100                 105                 110

Leu Val Thr Cys Ala Lys Phe Gln Cys Leu Glu Pro Ile Glu Gly Lys
            115                 120                 125

Val Val Gln His Glu Asn Leu Lys Tyr Thr Val Ile Ile Thr Val His
130                 135                 140

Thr Gly Asp Gln His Gln Val Gly Asn Glu Thr Gln Gly Val Thr Ala
145                 150                 155                 160

Glu Ile Thr Pro Gln Ala Ser Thr Ala Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

Glu Met Ile Leu Leu Thr Met Lys Asn Lys Ala Trp Met Val His Arg
        195                 200                 205

Gln Trp Phe Phe Asp Leu Pro Leu Pro Trp Thr Ser Gly Ala Thr Thr
    210                 215                 220

Glu Thr Pro Thr Trp Asn Arg Lys Glu Leu Leu Val Thr Phe Lys Asn
225                 230                 235                 240

Ala His Ala Lys Lys Gln Glu Val Val Leu Gly Ser Gln Glu Gly
                245                 250                 255

Ala Met His Thr Ala Leu Thr Gly Ala Thr Glu Ile Gln Asn Ser Gly
            260                 265                 270

Gly Thr Ser Ile Phe Ala Gly His Leu Lys Cys Arg Leu Lys Met Asp
        275                 280                 285

Lys Leu Glu Leu Lys Gly Met Ser Tyr Ala Met Cys Ser Asn Thr Phe
    290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
            340                 345                 350

Asn Pro Val Val Thr Lys Lys Glu Glu Pro Val Asn Ile Glu Ala Glu
        355                 360                 365

Pro Pro Phe Gly Glu Ser Asn Ile Val Ile Gly Ile Gly Asp Lys Ala
    370                 375                 380

Leu Lys Ile Asn Trp Tyr Lys Lys Gly Ser Ser Ile Gly Lys Met Phe
385                 390                 395                 400

Glu Ala Thr Ala Arg Gly Ala Arg Arg Met Ala Ile Leu Gly Asp Thr
                405                 410                 415

Ala Trp Asp Phe Gly Ser Val Gly Gly Val Leu Asn Ser Leu Gly Lys
            420                 425                 430

Met Val His Gln Ile Phe Gly Ser Ala Tyr Thr Ala Leu Phe Ser Gly
        435                 440                 445

Val Ser Trp Ile Met Lys Ile Gly Ile Gly Val Leu Leu Thr Trp Ile
    450                 455                 460

Gly Leu Asn Ser Lys Asn Thr Ser Met Ser Phe Ser Cys Ile Ala Ile
465                 470                 475                 480

Gly Ile Ile Thr Leu Tyr Leu Gly Ala Val Val Gln Ala
                485                 490

<210> SEQ ID NO 7
<211> LENGTH: 1488
```

```
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1)..(1488)
<223> OTHER INFORMATION: DENV-4 consensus E protein coding sequence
<220> FEATURE:
<221> NAME/KEY: misc_feature
<222>

| | | | | | | | | | | | | | | |
|---|---|---|---|---|---|---|---|---|---|---|---|---|---|---|
| gaa | gga | gcc | atg | cac | tct | gcc | ctc | acc | gga | gcc | aca | gaa | gtg | gat | tcc | 816 |
| Glu | Gly | Ala | Met | His | Ser | Ala | Leu | Thr | Gly | Ala | Thr | Glu | Val | Asp | Ser |
| | | | 260 | | | | | 265 | | | | | 270 | | |

```
gaa gga gcc atg cac tct gcc ctc acc gga gcc aca gaa gtg gat tcc    816
Glu Gly Ala Met His Ser Ala Leu Thr Gly Ala Thr Glu Val Asp Ser
            260                 265                 270 ggt gat gga aac cac atg ttt gca gga cac cta aag tgc aaa gta cgc    864
Gly Asp Gly Asn His Met Phe Ala Gly His Leu Lys Cys Lys Val Arg
        275                 280                 285 atg gaa aaa ttg aga atc aag gga atg tca tac acg atg tgc tca gga    912
Met Glu Lys Leu Arg Ile Lys Gly Met Ser Tyr Thr Met Cys Ser Gly
    290                 295                 300 aag ttc tca att gac aaa gag atg gca gaa aca cag cat gga aca aca    960
Lys Phe Ser Ile Asp Lys Glu Met Ala Glu Thr Gln His Gly Thr Thr
305                 310                 315                 320 gtg gtg aaa gtc aag tat gaa ggt act gga gct cca tgc aaa gtc ccc    1008
Val Val Lys Val Lys Tyr Glu Gly Thr Gly Ala Pro Cys Lys Val Pro
                325                 330                 335 ata gag ata aga gat gtg aac aag gaa aaa gtg gtt ggg cgc atc atc    1056
Ile Glu Ile Arg Asp Val Asn Lys Glu Lys Val Val Gly Arg Ile Ile
            340                 345                 350 tca tct acc cct ttt gct gag aat acc aac agt gta acc aat ata gaa    1104
Ser Ser Thr Pro Phe Ala Glu Asn Thr Asn Ser Val Thr Asn Ile Glu
        355                 360                 365 tta gaa ccc cct ttt ggg gac agc tac ata gtg ata ggt gtt gga gac    1152
Leu Glu Pro Pro Phe Gly Asp Ser Tyr Ile Val Ile Gly Val Gly Asp
    370                 375                 380 agt gca tta aca ctc cat tgg ttc agg aaa ggg agt tcc att ggc aag    1200
Ser Ala Leu Thr Leu His Trp Phe Arg Lys Gly Ser Ser Ile Gly Lys
385                 390                 395                 400 atg ttt gag tcc aca tac aga ggt gca aaa cga atg gcc att cta ggt    1248
Met Phe Glu Ser Thr Tyr Arg Gly Ala Lys Arg Met Ala Ile Leu Gly
                405                 410                 415 gaa aca gct tgg gat ttt ggt tcc gtt ggt gga ctg ttc aca tca tta    1296
Glu Thr Ala Trp Asp Phe Gly Ser Val Gly Gly Leu Phe Thr Ser Leu
            420                 425                 430 gga aaa gct gtg cac cag gtt ttt ggc agt gtc tac aca acc atg ttt    1344
Gly Lys Ala Val His Gln Val Phe Gly Ser Val Tyr Thr Thr Met Phe
        435                 440                 445 gga gga gtc tca tgg atg att aga atc cta atc ggg ttc tta gtg ttg    1392
Gly Gly Val Ser Trp Met Ile Arg Ile Leu Ile Gly Phe Leu Val Leu
    450                 455                 460 tgg atc ggc acg aac tca aga aac act tca atg gct atg acg tgc ata    1440
Trp Ile Gly Thr Asn Ser Arg Asn Thr Ser Met Ala Met Thr Cys Ile
465                 470                 475                 480 gct gtt gga gga atc acc ctg ttt ctg ggc ttc aca gtt caa gca taa    1488
Ala Val Gly Gly Ile Thr Leu Phe Leu Gly Phe Thr Val Gln Ala
                485                 490                 495

<210> SEQ ID NO 8
<211> LENGTH: 495
<212> TYPE: PRT
<213> ORGANISM: Artificial Sequence
<220> FEATURE:
<223> OTHER INFORMATION: Synthetic Construct

<400> SEQUENCE: 8

Met Arg Cys Val Gly Val Gly Asn Arg Asp Phe Val Glu Gly Val Ser
1               5                   10                  15

Gly Gly Ala Trp Val Asp Leu Val Leu Glu His Gly Gly Cys Val Thr
            20                  25                  30

Thr Met Ala Gln Gly Lys Pro Thr Leu Asp Phe Glu Leu Ile Lys Thr
        35                  40                  45
```

```
Thr Ala Lys Glu Val Ala Leu Leu Arg Thr Tyr Cys Ile Glu Ala Ser
    50              55                  60
Ile Ser Asn Ile Thr Thr Ala Thr Arg Cys Pro Thr Gln Gly Glu Pro
65              70                  75                  80
Tyr Leu Lys Glu Glu Gln Asp Gln Gln Tyr Ile Cys Arg Arg Asp Val
                85                  90                  95
Val Asp Arg Gly Trp Gly Asn Gly Cys Gly Leu Phe Gly Lys Gly Gly
            100                 105                 110
Val Val Thr Cys Ala Lys Phe Ser Cys Ser Gly Lys Ile Thr Gly Asn
            115                 120                 125
Leu Val Gln Ile Glu Asn Leu Glu Tyr Thr Val Val Thr Val His
130                 135                 140
Asn Gly Asp Thr His Ala Val Gly Asn Asp Thr Ser Asn His Gly Val
145                 150                 155                 160
Thr Ala Thr Ile Thr Pro Arg Ser Pro Ser Val Glu Val Lys Leu Pro
                165                 170                 175
Asp Tyr Gly Glu Leu Thr Leu Asp Cys Glu Pro Arg Ser Gly Ile Asp
            180                 185                 190
Phe Asn Glu Met Ile Leu Met Lys Met Lys Lys Lys Thr Trp Leu Val
            195                 200                 205
His Lys Gln Trp Phe Leu Asp Leu Pro Leu Pro Trp Thr Ala Gly Ala
210                 215                 220
Asp Thr Ser Glu Val His Trp Asn His Lys Glu Arg Met Val Thr Phe
225                 230                 235                 240
Lys Val Pro His Ala Lys Arg Gln Asp Val Thr Val Leu Gly Ser Gln
                245                 250                 255
Glu Gly Ala Met His Ser Ala Leu Thr Gly Ala Thr Glu Val Asp Ser
            260                 265                 270
Gly Asp Gly Asn His Met Phe Ala Gly His Leu Lys Cys Lys Val Arg
            275                 280                 285
Met Glu Lys Leu Arg Ile Lys Gly Met Ser Tyr Thr Met Cys Ser Gly
290                 295                 300
Lys Phe Ser Ile Asp Lys Glu Met Ala Glu Thr Gln His Gly Thr Thr
305                 310                 315                 320
Val Val Lys Val Lys Tyr Glu Gly Thr Gly Ala Pro Cys Lys Val Pro
                325                 330                 335
Ile Glu Ile Arg Asp Val Asn Lys Glu Lys Val Val Gly Arg Ile Ile
            340                 345                 350
Ser Ser Thr Pro Phe Ala Glu Asn Thr Asn Ser Val Thr Asn Ile Glu
            355                 360                 365
Leu Glu Pro Pro Phe Gly Asp Ser Tyr Ile Val Ile Gly Val Gly Asp
370                 375                 380
Ser Ala Leu Thr Leu His Trp Phe Arg Lys Gly Ser Ser Ile Gly Lys
385                 390                 395                 400
Met Phe Glu Ser Thr Tyr Arg Gly Ala Lys Arg Met Ala Ile Leu Gly
                405                 410                 415
Glu Thr Ala Trp Asp Phe Gly Ser Val Gly Gly Leu Phe Thr Ser Leu
            420                 425                 430
Gly Lys Ala Val His Gln Val Phe Gly Ser Val Tyr Thr Thr Met Phe
            435                 440                 445
Gly Gly Val Ser Trp Met Ile Arg Ile Leu Ile Gly Phe Leu Val Leu
450                 455                 460
Trp Ile Gly Thr Asn Ser Arg Asn Thr Ser Met Ala Met Thr Cys Ile
```

```
465                 470                 475                 480

Ala Val Gly Gly Ile Thr Leu Phe Leu Gly Phe Thr Val Gln Ala
                485                 490                 495

<210> SEQ ID NO 9
<211> LENGTH: 2064
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(6)
<223> OTHER INFORMATION: NheI restriction site
<220> FEATURE:
<221> NAME/KEY: misc_feature
<222> LOCATION: (7)..(16)
<223> OTHER INFORMATION: Kozak sequence
<220> FEATURE:
<221> NAME/KEY: misc_feature
<222> LOCATION: (13)..(570)
<223> OTHER INFORMATION: Signal sequence/prM coding sequence
<220> FEATURE:
<221> NAME/KEY: misc_feature
<222> LOCATION: (571)..(1764)
<223> OTHER INFORMATION: Ecto E coding sequence
<220> FEATURE:
<221> NAME/KEY: misc_feature
<222> LOCATION: (571)..(2058)
<223> OTHER INFORMATION: Consensus E protein coding sequence
<220> FEATURE:
<221> NAME/KEY: misc_feature
<222> LOCATION: (2059)..(2064)
<223> OTHER INFORMATION: XhoI restriction site
<400> SEQUENCE: 9
gctagcgcca ccatgaatag aagaaaaaga tccgtgacca tgctccttat gctgctgccc     60
acagccctgg cgttccatct gaccacacga gggggagagc cgcacatgat agttagcaag    120
caggaaagag gaaagtcact tttgtttaag acctctgcag gtgtcaacat gtgcaccctt    180
attgcgatgg atttgggaga gttatgtgag gacacaatga cctacaaatg cccccggatc    240
actgaggcgg aaccagatga cgttgattgt tggtgcaatg ccacggacac atgggtgacc    300
tatggaacgt gttctcaaac tggcgaacac cgacgagaca aacgttccgt cgcactggcc    360
ccacacgttg ggcttggtct agaaacaaga gccgaaacgt ggatgtcctc tgaaggcgct    420
tggaaacaaa tacaaaaagt ggagacttgg gctctgagac acccaggatt cacagtgata    480
gcccttttc tagcacatgc cataggaaca tccatcaccc agaaagggat tattttcatt    540
ttgttgatgc tggtaacacc atccatggcc atgcgatgcg tgggaatagg caacagagac    600
ttcgtggaag gactgtcagg agcaacgtgg gtggatgtgg tactggagca tggaagttgc    660
gtcaccacca tggcaaaaaa taaaccaaca ctggacattg aactcttgaa gacggaggtc    720
acaaaccctg ccgtcctgcg caaactgtgc attgaagcta aaatatcaaa caccaccacc    780
gattcaagat gtccaacaca aggagaagcc acactggtgg aagaacaaga cgcgaacttt    840
gtgtgccgac gaacgtttgt ggacagaggc tggggcaatg gctgtgggct attcggaaaa    900
ggtagcctaa taacgtgtgc taagtttaag tgtgtgacaa aactagaagg aaagatagtt    960
caatatgaaa acttaaaata ttcagtgata gtcaccgtcc acactggaga ccagcaccag   1020
gtgggaaatg agactacaga acatggaaca actgcaacca taacacctca agctcccacg   1080
tcggaaatac agctgaccga ctacggagct ctcacattgg attgttcacc tagaacaggg   1140
ctagacttta atgagatggt gttgttgaca atgaaagaaa aatcatggct tgtccacaaa   1200
```

-continued

```
caatggtttc tagacttacc actgccttgg acctcggggg cttcaacatc ccaagagact 1260
tggaacagac aagatttgct ggtcacattt aagacagctc atgcaaagaa gcaggaagta 1320
gtcgtactag gatcacaaga aggagcaatg cacactgcgt tgactggagc gacagaaatc 1380
caaacgtcag gaacgacaac aatttttgca ggacacctga aatgcagact aaaaatggat 1440
aaactgactt taaaagggat gtcatatgtg atgtgcacag gctcattcaa gttagagaaa 1500
gaagtggctg agacccagca tggaactgtt ctagtgcagg ttaaatacga aggaacagat 1560
gcaccatgca agatcccctt ttcgacccaa gatgagaaag gagtaaccca gaatgggaga 1620
ttgataacag ccaaccccat agtcactgac aaagaaaaac cagtcaacat tgaggcagaa 1680
ccaccttttg gtgagagcta catcgtggta ggagcaggtg aaaaagcttt gaaactaagc 1740
tggttcaaga aaggaagcag catagggaaa atgtttgaag caactgcccg aggagcacga 1800
aggatggcca tcctgggaga caccgcatgg gacttcggtt ctataggagg agtgttcacg 1860
tctgtgggaa aactggtaca ccagattttt ggaactgcat atggagtttt gttcagcggt 1920
gtttcttgga ccatgaaaat aggaataggg attctgctga catggctagg attaaattca 1980
aggagcacgt ccctttcgat gacgtgcatc gcagttggca tggtcacact gtacctagga 2040
gtcatggttc aggcgtgact cgag 2064
```

```
<210> SEQ ID NO 10
<211> LENGTH: 2067
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(6)
<223> OTHER INFORMATION: NheI restriction site
<220> FEATURE:
<221> NAME/KEY: misc_feature
<222> LOCATION: (7)..(16)
<223> OTHER INFORMATION: Kozak sequence
<220> FEATURE:
<221> NAME/KEY: misc_feature
<222> LOCATION: (13)..(570)
<223> OTHER INFORMATION: Signal sequence/prM coding sequence
<220> FEATURE:
<221> NAME/KEY: misc_feature
<222> LOCATION: (571)..(1764)
<223> OTHER INFORMATION: Ecto E coding sequence
<220> FEATURE:
<221> NAME/KEY: misc_feature
<222> LOCATION: (571)..(2058)
<223> OTHER INFORMATION: Consensus E protein coding sequence
<220> FEATURE:
<221> NAME/KEY: misc_feature
<222> LOCATION: (2059)..(2061)
<223> OTHER INFORMATION: stop codon
<220> FEATURE:
<221> NAME/KEY: misc_feature
<222> LOCATION: (2062)..(2067)
<223> OTHER INFORMATION: XhoI restriction site
<400> SEQUENCE: 10
gctagcgcca ccatgaacag gagacgcaga actgcaggca tgatcattat gctgattcca 60
acagtgatgg cgttccattt aaccacacgt aacggagaac cacacatgat cgtcagtaga 120
caagagaaag ggaaaagtct tctgtttaaa acagaggatg gtgtgaacat gtgtaccctc 180
atggccatgg accttggtga attgtgtgaa gatacaatca cgtacaagtg tccttttctc 240
aagcagaatg aaccagaaga catagattgt tggtgcaact ctacgtccac atgggtaact 300
tatgggacgt gtaccaccac aggagaacac agaagagaaa aaagatcagt ggcactcgtt 360
```

```
ccacatgtgg gaatgggact ggagacacga actgaaacat ggatgtcatc agaagggggcc    420 tggaaacatg cccagagaat tgaaacttgg atcttgagac atccaggctt taccataatg    480
gcagcaatcc tggcatacac cataggaacg acacatttcc aaagagccct gatttccatc    540
ttactgacag ctgtcgctcc ttcaatgaca atgcgttgca taggaatatc aaatagagac    600
tttgtagaag gggtttcagg aggaagctgg gttgacatag tcttagaaca tggaagctgt    660
gtgacgacga tggcaaaaaa caaaccaaca ttgattttg aactgataaa acagaagcc    720 aaacaacctg ccactctaag gaagtactgt atagaagcaa agctgaccaa cacaacaaca    780
gaatctcgct gcccaacaca aggggaaccc agcctaaatg aagagcagga caaaggttc    840 gtctgcaaac actccatggt agacagagga tggggaaatg gatgtggatt atttggaaaa    900
ggaggcattg tgacctgtgc tatgttcaca tgcaaaaaga acatggaagg aaaaatcgtg    960
caaccagaaa acttggaata caccatcgtg ataacacctc actcagggga gagcatgca   1020 gtcggaaatg acacaggaaa acatggcaag gaaatcaaaa taacaccaca gagttccatc   1080
acagaagcag aactgacagg ctatggcact gtcacgatgg agtgctctcc gagaacgggc   1140
ctcgacttca atgagatggt gttgctgcaa atggaaaaca aagcttggct ggtgcacagg   1200
caatggttcc tagacctgcc gttaccatgg ctgcccggag cggacacaca aggatcaaat   1260
tggatacaga aagagacatt ggtcactttc aaaaatcccc atgcgaagaa acaggatgtt   1320
gttgttttag atccccaaga aggggccatg cacacagcac tcacaggggc cacagaaatc   1380
cagatgtcat caggaaactt actgttcaca ggacatctca gtgcaggct gagaatggac   1440 aaactacagc tcaaaggaat gtcatactcc atgtgcacag gaaagtttaa agttgtgaag   1500
gaaatagcag aaacacaaca tggaacaata gttatcagag tacaatatga aggggacggc   1560
tctccatgta agatcccttt tgagataatg gatttggaaa aagacatgt cttaggtcgc   1620 ctgatcacag tcaacccaat tgtgacagaa aaagacagcc cagtcaacat agaagcagaa   1680
cctccattcg gagacagcta catcatcata ggagtagagc cgggacaact gaagctcaac   1740
tggtttaaga aggaagttc tatcggccaa atgtttgaga caacaatgag aggagcgaag   1800
agaatggcca ttttaggtga cacagcctgg gatttggat ccctggggagg agtgttcaca   1860 tctataggaa aagctctcca ccaagttttt ggagcaatct atgggctgc cttcagtggg   1920 gtctcatgga ctatgaaaat cctcatagga gtcatcatca catggatagg aatgaactca   1980
cgcagcacct cactgtctgt gtcactagta ttagtgggaa tcgtgacact gtacttggga   2040
gttatggtgc aggcctaata actcgag                                      2067
```

<210> SEQ ID NO 11
<211> LENGTH: 2064
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(6)
<223> OTHER INFORMATION: NheI restriction site
<220> FEATURE:
<221> NAME/KEY: misc_feature
<222> LOCATION: (7)..(16)
<223> OTHER INFORMATION: Kozak sequence
<220> FEATURE:
<221> NAME/KEY: misc_feature
<222> LOCATION: (13)..(573)
<223> OTHER INFORMATION: Signal sequence/prM coding sequence
<220> FEATURE:

<220> FEATURE:
<221> NAME/KEY: misc_feature
<222> LOCATION: (574)..(1761)
<223> OTHER INFORMATION: Ecto E coding sequence
<220> FEATURE:
<221> NAME/KEY: misc_feature
<222> LOCATION: (574)..(2064)
<223> OTHER INFORMATION: Consensus E protein coding sequence

<400> SEQUENCE: 11

```
gctagcgcca ccatgatcaa caaacggaaa aagacatcgc tctgtctcat gatgatgtta      60
ccagcaacac ttgctttcca cttaacttca cgagatggag agccgcgcat gattgtgggg     120
aagaatgaaa gaggaaaatc cctactttt aagacagcct ctggaatcaa catgtgcaca     180
ctcatagcca tggatttggg agagatgtgt gatgacacgg tcacttacaa atgcccccac     240
attaccgaag tggagcctga agacattgac tgttggtgca accttacatc gacatgggtg     300
acttatggaa catgcaatca agctggagag catagacgcg ataagagatc agtggcgtta     360
gctccccatg tcggcatggg actggacaca cgcactcaaa cctggatgtc ggctgaagga     420
gcttggagac aagtcgagaa ggtagagaca tgggcccta ggcacccagg gtttaccata     480
ctagccctat tcttgcccca ttacataggc acttccttga cccagaaagt ggttattttt     540
atactattaa tgctggttac cccatccatg acaatgagat gcgtgggagt aggaaacaga     600
gattttgtgg aaggcctatc aggagctacg tgggttgacg tggtgctcga gcacggtggg     660
tgtgtgacta ccatggctaa gaacaagccc acgctggaca tagagcttca gaagaccgag     720
gccacccaac tggcgaccct aaggaagcta tgcattgagg aaaaattac caacataaca     780
accgactcaa ggtgtcccac ccaagggaa gcgattttac ctgaggagca ggaccagaac     840
tacgtgtgta agcacacata cgtggacaga ggctggggaa acggttgtgg tttgtttggc     900
aagggaagct tggtaacatg cgcgaaattt caatgtctag accaataga gggaaaagtg     960
gtgcaacatg agaacctcaa atacaccgtc atcatcacag tgcacacagg agaccaacac    1020
caggtgggaa atgaaacgca gggagtcacg gctgagataa cacccaggc atcaaccgct    1080
gaagccatct acctgaata tggaacccct gggctagaat gctcaccacg gacaggtttg    1140
gatttcaatg aaatgatctt actaacaatg aagaacaaag catggatggt acatagacaa    1200
tggttctttg acctacctct accatggaca tcaggagcta caacagaaac accaacctgg    1260
aacaggaaag agcttcttgt gacattcaaa acgcacatg caaaaaaaca agaagtagtt    1320
gtccttggat cgcaagaggg agcaatgcac acagcactga caggagccac agagatccaa    1380
aactcaggag gcacaagtat ttttgcgggg cacttaaaat gtagacttaa gatgacaaa    1440
ttggaactca aggggatgag ctatgcaatg tgctcgaata cctttgtgtt gaagaaagaa    1500
gtctccgaaa cgcagcatgg gacaatactc attaaggttg agtacaaagg ggaagatgca    1560
ccttgcaaga ttcctttctc cacagaggat ggacaaggga agctcacaa tggcagactg    1620
atcacagcca cccagtggt gaccaagaag gaggagcctg tcaacattga ggctgaacct    1680
ccttttgggg aaagtaacat agtgattgga attgagaca aagccttgaa atcaactgg    1740
tacaagaagg gaagctcgat tgggaagatg ttcgaggcca ctgccagagg tgcaaggcgc    1800
atggccatct gggagacac agcctggac tttggatcag tggtggtgt tctaaactca    1860
ttaggaaaaa tggtgcacca atattcgga agtgcttaca cagccctatt tagtggagtc    1920
tcttggataa tgaaaattgg aataggtgtc ctcttaacct ggataggggtt gaattcaaaa    1980
aacacttcca tgtcattttc atgcattgcg ataggaatca ttacactcta tctgggagcc    2040
gtggtgcaag cttaatctag ataa                                           2064
```

<210> SEQ ID NO 12
<211> LENGTH: 2067
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(16)
<223> OTHER INFORMATION: Kozak sequence
<220> FEATURE:
<221> NAME/KEY: misc_feature
<222> LOCATION: (13)..(573)
<223> OTHER INFORMATION: Signal sequence/prM coding sequence
<220> FEATURE:
<221> NAME/KEY: misc_feature
<222> LOCATION: (574)..(1767)
<223> OTHER INFORMATION: Ecto E coding sequence
<220> FEATURE:
<221> NAME/KEY: misc_feature
<222> LOCATION: (574)..(2061)
<223> OTHER INFORMATION: Consensus E protein coding sequence
<220> FEATURE:
<221> NAME/KEY: misc_feature
<222> LOCATION: (2062)..(2067)
<223> OTHER INFORMATION: XbaI restriction site

<400> SEQUENCE: 12

```
gaattcgcca ccatgttgaa tgggagaaaa aggtcaacaa tgacattgct gtgcttgatt 60
cccaccgtaa tggcgtttca cttgtcaaca agagatggcg aaccccttat gatagtggca 120
aaacacgaaa gggggagacc tctcttgttt aagacaacag agggaatcaa caaatgcact 180
cttattgcca tggacctggg tgaaatgtgt gaggacaccg tcacgtatga gtgccctcta 240
ctggtcaata ccgaacctga ggacattgat tgctggtgca atctcacgtc tgcgtgggtc 300
atgtatggga catgcactca gagtggggaa cggagacggg agaagcgctc agtagcccta 360
acaccacatt caggaatggg attggagaca agggctgaga catggatgtc atcggaaggg 420
gcttggaaac atgctcagag ggtagagagt tggatactca gaaacccagg attcgctctc 480
ttggcaggat ttatggccta tatgattggg caaacaggaa tccagcgaac agtcttcttt 540
gttctaatga tgctggtcgc ccccatcctac ggaatgcgat gcgtaggagt agggaacaga 600
gactttgtgg aaggagtctc aggtggagca tgggtcgacc tggtgctaga acacggagga 660
tgtgtcacaa ccatggccca gggaaaacca accttggatt ttgaactgat caagacaaca 720
gccaaggaag tggctctgtt aagaacctat tgcattgaag cctcaatatc aaacataacc 780
acggcaacaa gatgtccaac gcaaggagaa ccttatctca aagaggaaca agaccaacag 840
tacatttgcc ggagagacgt ggtagacaga gggtggggca atggctgtgg cctgtttgga 900
aaaggaggag ttgtgacatg tgcaaagttt tcatgctcgg ggaagataac aggcaacttg 960
gtccaaattg aaaaccttga atacacagtg gttgtaacag tccacaatgg agacacccac 1020
gcagtaggaa atgacacatc caaccatgga gtgacagcca cgataacccc caggtcacca 1080
tcggtggaag ttaaattacc ggactatgga gaactaacac tcgattgtga acccaggtcc 1140
ggaattgact ttaatgagat gattctgatg aaaatgaaaa agaaaacatg gctcgtgcac 1200
aagcaatggt ttttggatct acctctgcca tggacagcag gagcagacac atcagaagtc 1260
cactggaatc acaaagagag aatggtgaca ttcaaggttc ctcatgccaa gagacaggat 1320

-continued

```
gtgacagtgc taggatctca ggaaggagcc atgcactctg ccctcaccgg agccacagaa   1380
gtggattccg gtgatggaaa ccacatgttt gcaggacacc taaagtgcaa agtacgcatg   1440
gaaaaattga aatcaaggg aatgtcatac acgatgtgct caggaaagtt ctcaattgac    1500
aaagagatgg cagaaacaca gcatggaaca acagtggtga agtcaagta tgaaggtact    1560 ggagctccat gcaaagtccc catagagata agagatgtga caaggaaaa agtggttggg    1620 cgcatcatct catctacccc ttttgctgag aataccaaca gtgtaaccaa tatagaatta   1680
gaaccccctt ttggggacag ctacatagtg ataggtgttg agacagtgc attaacactc     1740 cattggttca ggaagggag ttccattggc aagatgtttg agtccacata cagaggtgca    1800
aaacgaatgg ccattctagg tgaaacagct tgggatttg gttccgttgg tggactgttc    1860
acatcattag gaaaagctgt gcaccaggtt tttggcagtg tctacacaac catgtttgga   1920
ggagtctcat ggatgattag aatcctaatc gggttcttag tgttgtggat cggcacgaac   1980
tcaagaaaca cttcaatggc tatgacgtgc atagctgttg gaggaatcac cctgtttctg    2040
ggcttcacag ttcaagcata atctaga                                       2067
```

<210> SEQ ID NO 13
<211> LENGTH: 312
<212> TYPE: DNA
<213> ORGANISM: Dengue virus type 1
<220> FEATURE:
<221> NAME/KEY: CDS
<222> LOCATION: (1)..(312)
<223> OTHER INFORMATION: DIII domain

<400> SEQUENCE: 13

```
gct agc aag ggc atg agc tac gtg atg tgc acc ggc agc ttc aag ctg        48
Ala Ser Lys Gly Met Ser Tyr Val Met Cys Thr Gly Ser Phe Lys Leu
1               5                   10                  15 gaa aaa gag gtg gcc gag acc cag cac ggc acc gtc ctg gtg cag gtc        96
Glu Lys Glu Val Ala Glu Thr Gln His Gly Thr Val Leu Val Gln Val
            20                  25                  30 aag tac gag ggc acc gac gcc ccc tgc aag atc ccc ttc agc acc cag       144
Lys Tyr Glu Gly Thr Asp Ala Pro Cys Lys Ile Pro Phe Ser Thr Gln
        35                  40                  45 gac gag aag ggc gtg aca cag aac ggc agg ctg atc acc gcc aac ccc       192
Asp Glu Lys Gly Val Thr Gln Asn Gly Arg Leu Ile Thr Ala Asn Pro
    50                  55                  60 atc gtg acc gac aaa gag aag ccc gtc aac atc gag gcc gag ccc ccc       240
Ile Val Thr Asp Lys Glu Lys Pro Val Asn Ile Glu Ala Glu Pro Pro
65                  70                  75                  80 ttc ggc gag aac tac atc gtg gtg ggc gct ggc gag aag gcc ctg aag       288
Phe Gly Glu Asn Tyr Ile Val Val Gly Ala Gly Glu Lys Ala Leu Lys
                85                  90                  95 ctg tcc tgg ttc aag aag gga tcc                                       312
Leu Ser Trp Phe Lys Lys Gly Ser
            100
```

<210> SEQ ID NO 14
<211> LENGTH: 104
<212> TYPE: PRT
<213> ORGANISM: Dengue virus type 1

<400> SEQUENCE: 14

Ala Ser Lys Gly Met Ser Tyr Val Met Cys Thr Gly Ser Phe Lys Leu
1               5                   10                  15

Glu Lys Glu Val Ala Glu Thr Gln His Gly Thr Val Leu Val Gln Val
            20                  25                  30

```
Lys Tyr Glu Gly Thr Asp Ala Pro Cys Lys Ile Pro Phe Ser Thr Gln
            35                  40                  45

Asp Glu Lys Gly Val Thr Gln Asn Gly Arg Leu Ile Thr Ala Asn Pro
        50                  55                  60

Ile Val Thr Asp Lys Glu Lys Pro Val Asn Ile Glu Ala Glu Pro Pro
 65                 70                  75                  80

Phe Gly Glu Asn Tyr Ile Val Val Gly Ala Gly Glu Lys Ala Leu Lys
                85                  90                  95

Leu Ser Trp Phe Lys Lys Gly Ser
            100

<210> SEQ ID NO 15
<211> LENGTH: 312
<212> TYPE: DNA
<213> ORGANISM: Dengue virus type 2
<220> FEATURE:
<221> NAME/KEY: CDS
<222> LOCATION: (1)..(312)
<223> OTHER INFORMATION: DIII domain

<400> SEQUENCE: 15 gct agc aag ggc atg agc tac agc atg tgc acc ggc aag ttc aag gtg       48
Ala Ser Lys Gly Met Ser Tyr Ser Met Cys Thr Gly Lys Phe Lys Val
 1               5                  10                  15 gtg aaa gag atc gcc gag acc cag cac ggc acc atc gtg atc agg gtg       96
Val Lys Glu Ile Ala Glu Thr Gln His Gly Thr Ile Val Ile Arg Val
                20                  25                  30 cag tac gag ggc gac ggc agc ccc tgc aag atc ccc ttc gag atc atg      144
Gln Tyr Glu Gly Asp Gly Ser Pro Cys Lys Ile Pro Phe Glu Ile Met
            35                  40                  45 gac ctg gaa aag agg cac gtc ctg ggc agg ctg atc acc gtg aac ccc      192
Asp Leu Glu Lys Arg His Val Leu Gly Arg Leu Ile Thr Val Asn Pro
        50                  55                  60 atc gtg acc gag aag gac agc ccc gtg aac atc gag gcc gag ccc ccc      240
Ile Val Thr Glu Lys Asp Ser Pro Val Asn Ile Glu Ala Glu Pro Pro
 65                 70                  75                  80 ttc ggc gac agc tac atc atc atc ggc gtg gag ccc ggc cag ctg aag      288
Phe Gly Asp Ser Tyr Ile Ile Ile Gly Val Glu Pro Gly Gln Leu Lys
                85                  90                  95 ctg aac tgg ttc aag aag gga tcc                                      312
Leu Asn Trp Phe Lys Lys Gly Ser
            100

<210> SEQ ID NO 16
<211> LENGTH: 104
<212> TYPE: PRT
<213> ORGANISM: Dengue virus type 2

<400> SEQUENCE: 16

Ala Ser Lys Gly Met Ser Tyr Ser Met Cys Thr Gly Lys Phe Lys Val
 1               5                  10                  15

Val Lys Glu Ile Ala Glu Thr Gln His Gly Thr Ile Val Ile Arg Val
                20                  25                  30

Gln Tyr Glu Gly Asp Gly Ser Pro Cys Lys Ile Pro Phe Glu Ile Met
            35                  40                  45

Asp Leu Glu Lys Arg His Val Leu Gly Arg Leu Ile Thr Val Asn Pro
        50                  55                  60

Ile Val Thr Glu Lys Asp Ser Pro Val Asn Ile Glu Ala Glu Pro Pro
 65                 70                  75                  80
```

Phe Gly Asp Ser Tyr Ile Ile Ile Gly Val Glu Pro Gly Gln Leu Lys
                85                  90                  95

Leu Asn Trp Phe Lys Lys Gly Ser
            100

<210> SEQ ID NO 17
<211> LENGTH: 312
<212> TYPE: DNA
<213> ORGANISM: Dengue virus type 3
<220> FEATURE:
<221> NAME/KEY: CDS
<222> LOCATION: (1)..(312)
<223> OTHER INFORMATION: DIII domain

<400> SEQUENCE: 17

```
gct agc aag ggc atg agc tac gcc atg tgc ctg aac acc ttc gtg ctg      48
Ala Ser Lys Gly Met Ser Tyr Ala Met Cys Leu Asn Thr Phe Val Leu
1               5                   10                  15 aag aaa gag gtc tcc gag acc cag cac ggc acc atc ctg atc aag gtg      96
Lys Lys Glu Val Ser Glu Thr Gln His Gly Thr Ile Leu Ile Lys Val
            20                  25                  30 gag tac aag ggc gag gac gcc ccc tgc aag atc ccc ttc agc acc gag     144
Glu Tyr Lys Gly Glu Asp Ala Pro Cys Lys Ile Pro Phe Ser Thr Glu
        35                  40                  45 gac ggc cag ggc aag gct cac aac ggc agg ctg atc acc gcc aac ccc     192
Asp Gly Gln Gly Lys Ala His Asn Gly Arg Leu Ile Thr Ala Asn Pro
    50                  55                  60 gtg gtg acc aag aaa gag gaa ccc gtc aac atc gag gcc gag ccc ccc     240
Val Val Thr Lys Lys Glu Glu Pro Val Asn Ile Glu Ala Glu Pro Pro
65                  70                  75                  80 ttc ggc gag agc aac atc gtg atc ggc atc ggc gac aag gcc ctg aag     288
Phe Gly Glu Ser Asn Ile Val Ile Gly Ile Gly Asp Lys Ala Leu Lys
                85                  90                  95 atc aac tgg tac agg aag gga tcc                                     312
Ile Asn Trp Tyr Arg Lys Gly Ser
            100
```

<210> SEQ ID NO 18
<211> LENGTH: 104
<212> TYPE: PRT
<213> ORGANISM: Dengue virus type 3

<400> SEQUENCE: 18

Ala Ser Lys Gly Met Ser Tyr Ala Met Cys Leu Asn Thr Phe Val Leu
1               5                   10                  15

Lys Lys Glu Val Ser Glu Thr Gln His Gly Thr Ile Leu Ile Lys Val
            20                  25                  30

Glu Tyr Lys Gly Glu Asp Ala Pro Cys Lys Ile Pro Phe Ser Thr Glu
        35                  40                  45

Asp Gly Gln Gly Lys Ala His Asn Gly Arg Leu Ile Thr Ala Asn Pro
    50                  55                  60

Val Val Thr Lys Lys Glu Glu Pro Val Asn Ile Glu Ala Glu Pro Pro
65                  70                  75                  80

Phe Gly Glu Ser Asn Ile Val Ile Gly Ile Gly Asp Lys Ala Leu Lys
                85                  90                  95

Ile Asn Trp Tyr Arg Lys Gly Ser
            100

<210> SEQ ID NO 19
<211> LENGTH: 309
<212> TYPE: DNA
<213> ORGANISM: Dengue virus type 4
<220> FEATURE:
<221> NAME/KEY: CDS
<222> LOCATION: (1)..(309)
<223> OTHER INFORMATION: DIII domain

<400> SEQUENCE: 19

| gct agc aag ggc atg agc tac acc atg tgc agc ggc aag ttc agc atc | 48 |
|---|---|
| Ala Ser Lys Gly Met Ser Tyr Thr Met Cys Ser Gly Lys Phe Ser Ile | |
| 1               5                   10                  15 | |

| gac aaa gag atg gcc gag acc cag cac ggc acc acc gtg gtg aag gtc | 96 |
|---|---|
| Asp Lys Glu Met Ala Glu Thr Gln His Gly Thr Thr Val Val Lys Val | |
|             20                  25                  30 | |

| aag tac gag ggc gct ggc gcc cct tgc aag gtg ccc atc gag atc agg | 144 |
|---|---|
| Lys Tyr Glu Gly Ala Gly Ala Pro Cys Lys Val Pro Ile Glu Ile Arg | |
|         35                  40                  45 | |

| gac gtg aac aaa gag aag gtc gtc ggc agg atc atc agc ccc acc ccc | 192 |
|---|---|
| Asp Val Asn Lys Glu Lys Val Val Gly Arg Ile Ile Ser Pro Thr Pro | |
|     50                  55                  60 | |

| ttc gcc gag aac acc aac agc gtg acc aac atc gag ctg gaa agg ccc | 240 |
|---|---|
| Phe Ala Glu Asn Thr Asn Ser Val Thr Asn Ile Glu Leu Glu Arg Pro | |
| 65                  70                  75                  80 | |

| ctg gac agc tac atc gtg atc ggc gtc ggc gac tct gcc ctg acc ctg | 288 |
|---|---|
| Leu Asp Ser Tyr Ile Val Ile Gly Val Gly Asp Ser Ala Leu Thr Leu | |
|                 85                  90                  95 | |

| cac tgg ttc agg aag gga tcc | 309 |
|---|---|
| His Trp Phe Arg Lys Gly Ser | |
|             100 | |

<210> SEQ ID NO 20
<211> LENGTH: 103
<212> TYPE: PRT
<213> ORGANISM: Dengue virus type 4

<400> SEQUENCE: 20

Ala Ser Lys Gly Met Ser Tyr Thr Met Cys Ser Gly Lys Phe Ser Ile
1               5                   10                  15

Asp Lys Glu Met Ala Glu Thr Gln His Gly Thr Thr Val Val Lys Val
            20                  25                  30

Lys Tyr Glu Gly Ala Gly Ala Pro Cys Lys Val Pro Ile Glu Ile Arg
        35                  40                  45

Asp Val Asn Lys Glu Lys Val Val Gly Arg Ile Ile Ser Pro Thr Pro
    50                  55                  60

Phe Ala Glu Asn Thr Asn Ser Val Thr Asn Ile Glu Leu Glu Arg Pro
65                  70                  75                  80

Leu Asp Ser Tyr Ile Val Ile Gly Val Gly Asp Ser Ala Leu Thr Leu
                85                  90                  95

His Trp Phe Arg Lys Gly Ser
            100

<210> SEQ ID NO 21
<211> LENGTH: 28
<212> TYPE: PRT
<213> ORGANISM: Artificial Sequence
<220> FEATURE:
<223> OTHER INFORMATION: Synthetic polypeptide (P28 region of C3d)

-continued

```
<400> SEQUENCE: 21

Lys Phe Leu Thr Thr Ala Lys Asp Lys Asn Arg Trp Glu Asp Pro Gly
1               5                   10                  15

Lys Gln Leu Tyr Asn Val Glu Ala Thr Ser Tyr Ala
            20                  25
```